(12) United States Patent
Gopinath et al.

(10) Patent No.: US 11,125,748 B2
(45) Date of Patent: Sep. 21, 2021

(54) METHOD FOR ORGANIZING INDIVIDUAL MOLECULES ON A PATTERNED SUBSTRATE AND STRUCTURES ASSEMBLED THEREBY

(71) Applicants: CALIFORNIA INSTITUTE OF TECHNOLOGY, Pasadena, CA (US); UNIVERSITY OF BRITISH COLUMBIA, Vancouver (CA)

(72) Inventors: Ashwin Gopinath, Cambridge, MA (US); Christopher Thachuk, Seattle, WA (US); David G. Kirkpatrick, Vancouver (CA); Paul W. Rothemund, Pasadena, CA (US)

(73) Assignees: UNIVERSITY OF BRITISH COLUMBIA, Vancouver (CA); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 166 days.

(21) Appl. No.: 16/121,603

(22) Filed: Sep. 4, 2018

(65) Prior Publication Data
US 2020/0025752 A1    Jan. 23, 2020

Related U.S. Application Data

(60) Provisional application No. 62/553,306, filed on Sep. 1, 2017.

(51) Int. Cl.
| | |
|---|---|
| *C12Q 1/68* | (2018.01) |
| *G01N 33/548* | (2006.01) |
| *G01N 21/64* | (2006.01) |
| *G01N 33/543* | (2006.01) |
| *C40B 50/18* | (2006.01) |

(52) U.S. Cl.
CPC ....... *G01N 33/548* (2013.01); *G01N 21/6428* (2013.01); *G01N 21/6445* (2013.01); *G01N 33/54373* (2013.01); *C40B 50/18* (2013.01)

(58) Field of Classification Search
CPC ......... C40B 20/02; C40B 40/06; C40B 50/18; C12Q 2525/30; C12N 2310/15; G01N 33/54366; G01N 33/551
See application file for complete search history.

(56) References Cited

U.S. PATENT DOCUMENTS

| | | | |
|---|---|---|---|
| 2007/0099208 A1* | 5/2007 | Drmanac | G01N 15/1404 435/6.12 |
| 2016/0102344 A1* | 4/2016 | Niemeyer | C12Q 2565/501 506/9 |

OTHER PUBLICATIONS

Kershner et al "PLacement and orientation of indiidual DNA shapes on lithographically patterned surfaces" Nature Nanotechnology, 2009, 4: 557-561. (Year: 2009).*

(Continued)

*Primary Examiner* — Betty J Forman
(74) *Attorney, Agent, or Firm* — Lewis Roca Rothgerber Christie LLP

(57) ABSTRACT

According to one embodiment of the present invention, a structure includes: a substrate having a patterned surface of one or more binding sites; and a molecular shape made by a polynucleotide platform having a shape corresponding to a shape of a binding site of the one or more binding sites, the molecular shape being bound to one of the one or more binding sites.

5 Claims, 29 Drawing Sheets
(23 of 29 Drawing Sheet(s) Filed in Color)

(56) References Cited

OTHER PUBLICATIONS

Wang et al "Controlling the shape, orientation, and linkage of carbon nanotube features with nano affinity templates" PNAS, 2006, 103:2026-2031. (Year: 2006).*
Gopinath, Ashwin, et al. "Absolute and arbitrary orientation of single-molecule shapes." *Science* 371.6531 (2021), 10 pages.
Gopinath, Ashwin, et al., "Absolute and arbitrary orientation of single molecule shapes." arXiv:1808.04544v1 [physics.app-ph], Aug. 14, 2018, 32 pages.

* cited by examiner

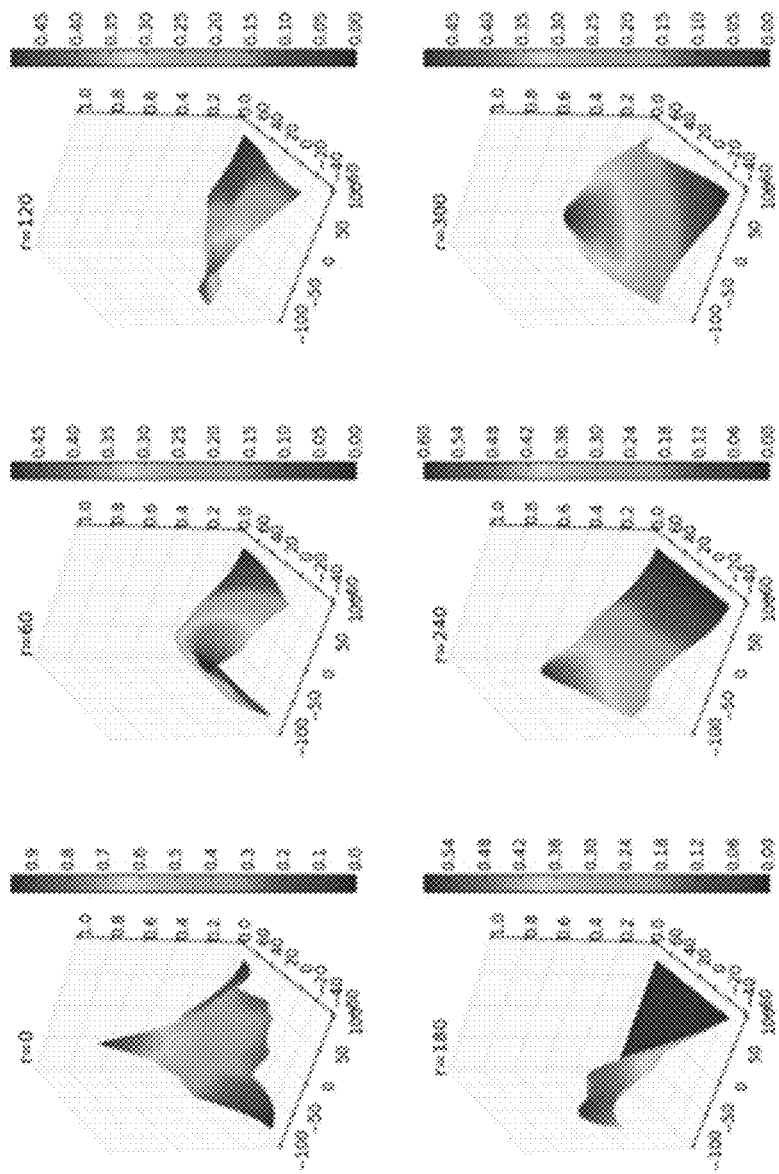
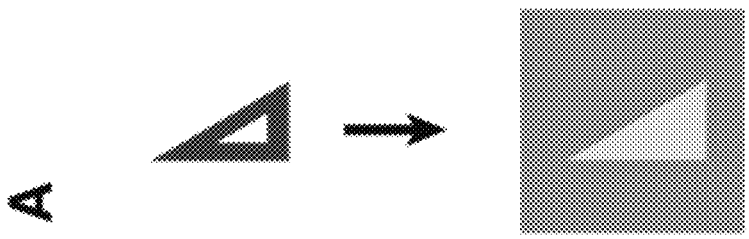
FIG. 8A

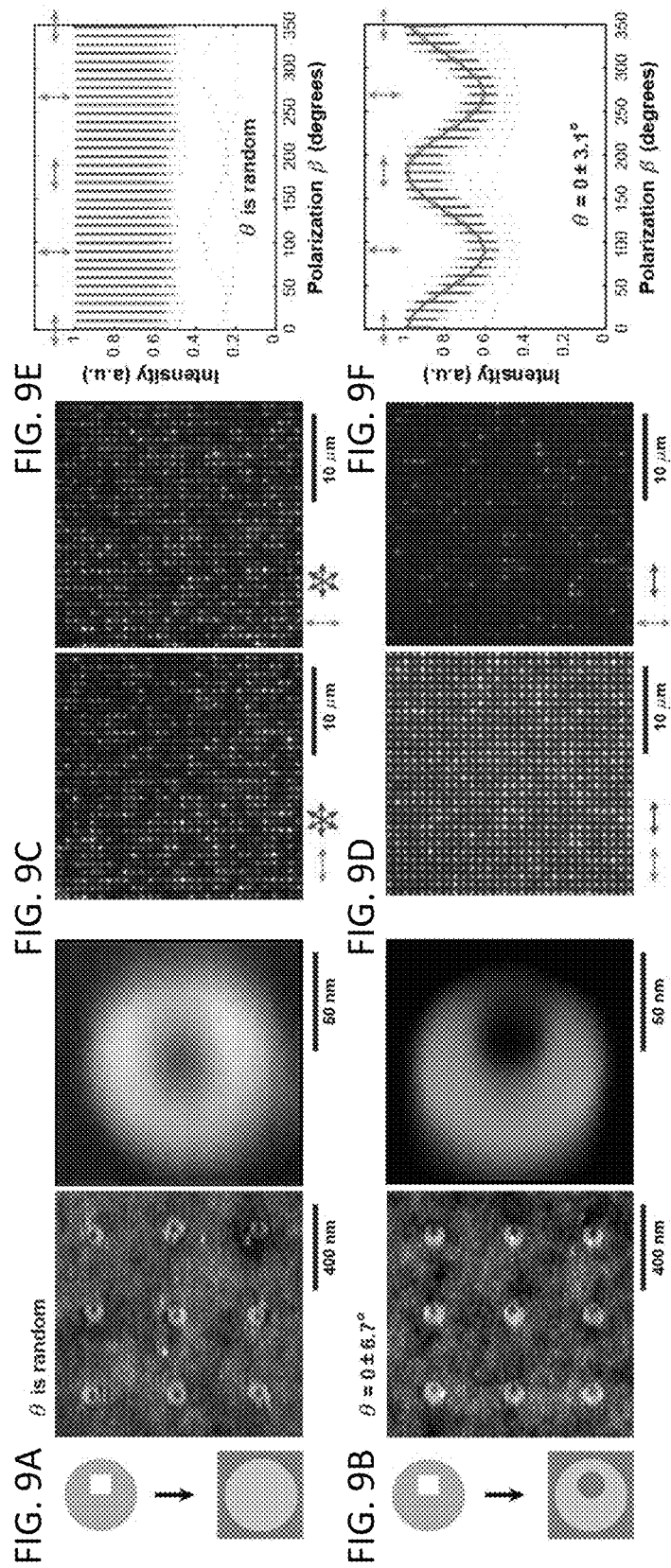

FIG. 19A
FIG. 19B
FIG. 19C
FIG. 19D
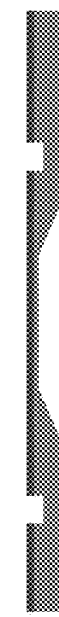
FIG. 19E
FIG. 19F
FIG. 19G
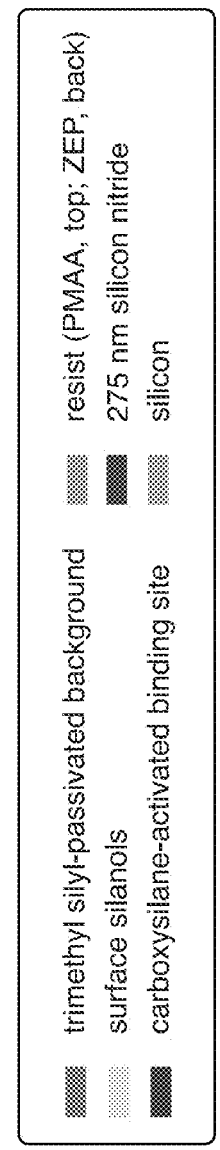

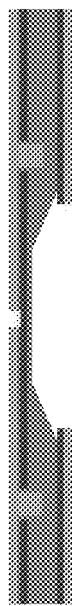
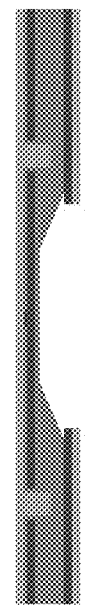
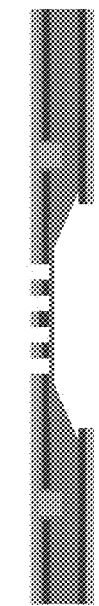
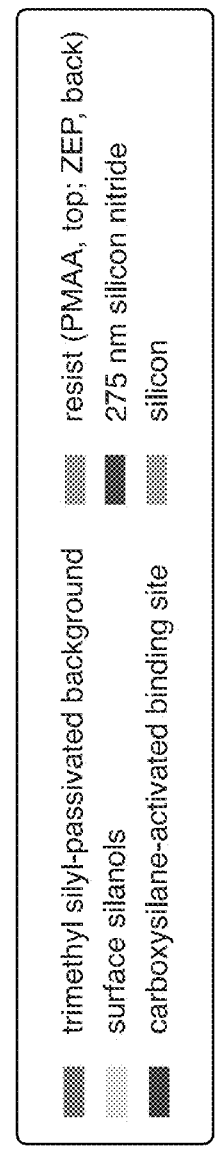
FIG. 19H  FIG. 19I  FIG. 19J  FIG. 19K  FIG. 19L  FIG. 19M  FIG. 19N

METHOD FOR ORGANIZING INDIVIDUAL MOLECULES ON A PATTERNED SUBSTRATE AND STRUCTURES ASSEMBLED THEREBY

CROSS-REFERENCE TO RELATED APPLICATION(S)

This application claims the benefit of U.S. Provisional Patent Application No. 62/553,306 "LITHOGRAPHIC ORGANIZATION OF INDIVIDUAL MOLECULES" filed in the United States Patent and Trademark Office on Sep. 1, 2017, the entire disclosure of which is incorporated by reference herein.

STATEMENT REGARDING FEDERALLY SPONSORED RESEARCH OR DEVELOPMENT

This invention was made with government support under Grant No. CCF1317694 & CMMI1636364 awarded by the National Science Foundation and under Grant No. N00014-14-1-0702 awarded by the Office of Naval Research and under Grant No. FA9550-16-1-0019 awarded by the Air Force. The government has certain rights in this invention.

FIELD

Aspects of embodiments of the present invention relate to the field of nanotechnology, including controlling the position and orientation of deoxyribonucleic acid (DNA) origami, and any attached structures, on the surface of lithographically patterned substrates.

BACKGROUND

Deoxyribonucleic Acid (DNA) is a biological molecule that is composed of two chains of nucleotides that form a double helix. In living organisms, DNA carries genetic instructions to control, for example, the growth, development, functioning, and reproduction of those organisms.

In some fields, such as synthetic biology and nanotechnology, DNA has found use as a material for constructing nanometer-scale structures or "molecular shapes." One such class of molecular shapes is scaffolded DNA origami, in which a long strand of single stranded DNA (a "scaffold" strand) is folded into a designed shape. In particular, in DNA origami, shorter strands of single stranded DNA ("staple" strands) are rationally designed to bind (through DNA base pairing interactions) to particular portions of the scaffold DNA, such that the staple strands bring together two different parts of the scaffold strand. Accordingly, an appropriately designed set of staple strands can fold the scaffold strand into various shapes, such as squares, stars, triangles, and disks with three-holes. See, for example, Rothemund, Paul WK. "Folding DNA to create nanoscale shapes and patterns." Nature 440.7082 (2006): 297 and associated Supplementary Notes 1-11 and Supplementary Note 12, the entire disclosures of which are incorporated by reference herein.

Multiple DNA origami may be combined to form larger or more complex structures. For example, six square DNA origami may be designed such that their edges bind to one another, thereby forming a cube. In addition, various techniques for attaching non-DNA molecules or particles to DNA are with DNA origami, thereby allowing DNA origami molecules (e.g., selected ones of the staple strands) to be combined with, for example, fluorescent tags, gold nanoparticles, functional groups, and antibodies.

SUMMARY

Aspects of embodiments of the present invention relate to systems and methods for controlling the positioning and orientation of a molecular shape generated using a polynucleotide platform capable of forming well-defined shapes in two or three dimensions, e.g. including but not limited to scaffolded deoxyribonucleic acid (DNA) origami (Rothemund, Paul WK. "Folding DNA to create nanoscale shapes and patterns", Nature 440.7082 (2006): 297), and any attached structures or devices, on the surface of lithographically patterned and unpatterned substrates.

According to one embodiment of the present invention, a structure includes: a substrate having a patterned surface of one or more binding sites and a nonbinding background, each of the one or more binding sites having: a shape that is rotationally asymmetric around an axis perpendicular to the patterned surface; and a first orientation direction defined along the plane of the patterned surface and relative to the shape of the binding site, the first orientation direction being independently defined, relative to the substrate, for each binding site of the one or more binding sites; and a molecular shape made by a polynucleotide platform having: a shape corresponding to the shape of the binding site; and a second orientation direction defined relative to the shape of the molecular shape, the molecular shape having a higher binding affinity for the one or more binding sites with the second orientation direction aligned with the first orientation direction than for the nonbinding background.

The shape may be a disk with an offset hole. The offset hole of the shape of the one or more binding sites may be circular. The area of the offset hole may be about 15% of the area of the disk. The offset hole of the shape of the molecular shape may be rectangular. The offset hole of the shape of the one or more binding sites may be circular, and the offset hole of the one or more binding sites may circumscribe the offset hole of the molecular shape.

An energy landscape of binding energy between the molecular shape and the one or more binding sites may have a single maximum.

The molecular shape may include a plurality of faces including a binding face and one or more non-binding faces, and the binding face of the molecular shape may have a higher binding affinity for the one or more binding sites than the non-binding faces.

The structure may include a photonic crystal cavity, the molecular shape may include a fluorophore having an electromagnetic dipole rigidly oriented with respect to the second orientation direction of the molecular shape, and the one or more binding sites may be located at independently defined positions within the photonic crystal cavity.

The structure may include a polarimeter, wherein each of a plurality of molecular shapes may include at least one fluorophore having a dipole rigidly oriented with respect to the second orientation direction of the molecular shape, and wherein the binding sites may be arranged into a plurality of contiguous arrays, each array having a different and independently defined array orientation, each of the binding sites in an array having a same first orientation aligned with the array orientation of the corresponding array.

According to one embodiment of the present invention, a structure includes: a substrate having a patterned surface of one or more binding sites; and a molecular shape made by a polynucleotide platform, the molecular shape being bound to one of the one or more binding sites, wherein the molecular shape includes a plurality of faces comprising a binding face and one or more non-binding faces, wherein the one or more binding sites have a higher binding affinity for the binding face than for the one or more non-binding faces.

The patterned surface of the substrate at the one or more binding sites may include: silanols; carboxylate groups; negatively charged functional groups; negatively charged polymers; or an inherent negative charge, wherein the binding face of the molecular shape may have an unmodified phosphate backbone in the presence of a multivalent cation. At least one of the one or more non-binding faces of the molecular shape may have: a plurality of single stranded DNA extensions; a neutral polymer; a zwitterionic coating; or combinations thereof. The patterned surface of the substrate may have a nonbinding background including: trimethyl silyl groups; neutral functional groups; a neutral polymer; a zwitterionic coating; or combinations thereof.

The patterned surface of the one or more binding sites may be: inherently negatively charged; modified with negatively charged functional groups; modified with a negatively-charged polymers; or combinations thereof. The binding face of the molecular shape may be: modified with amine groups; or modified with positively charged groups. At least one of the one or more non-binding faces of the molecular shape may have: an unmodified phosphate backbone; a plurality of single stranded DNA extensions; a neutral polymer; a zwitterionic coating; or combinations thereof. The patterned surface of the substrate may have a nonbinding background, and the nonbinding background may include: positive functional groups; neutral functional groups; a neutral polymer; a zwitterionic coating; or combinations thereof.

The patterned surface of the one or more binding sites may be: inherently positively charged; modified with a positively charged small molecule; modified with a positively charged polymer; modified with amine groups; or combinations thereof. The binding face of the molecular shape may be: unmodified to expose a phosphate backbone of the molecular shape; modified with a plurality of single stranded DNA extensions; modified with a negatively charged small molecule; modified with a negatively charged polymer; or combinations thereof. At least one of the one or more non-binding faces of the molecular shape may be modified with: a neutral polymer coating; or a zwitterionic coating. The patterned surface of the substrate may have a nonbinding background including: negative functional groups; neutral functional groups; a neutral polymer; a zwitterionic coating; or combinations thereof.

The one or more binding sites may include a catechol-binding material, the binding face of the molecular shape may be modified with a catechol, and the patterned surface of the substrate may have a nonbinding background that is inherently non-catechol binding or modified so that it does not bind a catechol. At least one of the one or more non-binding faces of the molecular shape may be: unmodified to expose a phosphate backbone of the molecular shape; modified with a plurality of single stranded DNA extensions; modified with a neutral polymer; modified with a zwitterionic coating; or combinations thereof.

The patterned surface of the one or more binding sites may be modified with thiol groups capable of forming covalent bonds. The binding face of the molecular shape may be: modified with a thiol group; modified with a maleimide group; modified with a vinyl group; or combinations thereof. At least one of the one or more non-binding faces of the molecular shape may be: modified with a plurality of single stranded DNA extensions; a zwitterionic coating; or a neutral polymer coating.

The patterned surface of the one or more binding sites may be modified with a noble metal. The binding face of the molecular shape may be: modified with a thiol group; modified with a phosphorothioate backbone; modified with coating plurality of single stranded DNA extensions; or combinations thereof. At least one of the one or more non-binding faces of the molecular shape may be: unmodified to expose a phosphate backbone of the molecular shape; modified with a repelling polymer coating including: weakly-gold binding single stranded DNA; double-stranded DNA; a neutral polymer; a zwitterionic coating; or combinations thereof; or combinations thereof. The patterned surface of the substrate may have a nonbinding background including a noble metal modified with: a thiolated neutral polymer; or a thiolated zwitterionic compound.

The patterned surface of the one or more binding sites may be a hydrophobic material. The hydrophobic material may be: graphene; boron nitride; molybdenum disulfide; or a two-dimensional and layered material. The binding face of the molecular shape may be modified with a polymer coating of single stranded DNA. At least one of the one or more non-binding faces of the molecular shape may be: unmodified to expose a phosphate backbone of the molecular shape; modified with a neutral polymer coating; modified with a zwitterionic coating; or combinations thereof. The patterned surface of the substrate may have a nonbinding background, and the nonbinding background of the substrate may be: modified with negatively charged groups; modified with a neutral polymer; or modified with a zwitterionic coating.

At least one of the binding sites may be large enough to bind a plurality of molecular shapes. The at least one of the one or more binding sites may encompass the entirety of the substrate, and the molecular shapes may control the density of a molecule of interest on the patterned surface of the substrate.

The molecular shape may have a shape corresponding to a shape of a binding site of the one or more binding sites.

According to one embodiment of the present invention, a method for orienting molecular shapes on a substrate includes: patterning a surface of a substrate with one or more binding sites and a nonbinding background to form a patterned surface, each binding site of the one or more binding sites having: a shape that is rotationally asymmetric around an axis perpendicular to the surface of the substrate; and an independently-defined first orientation direction along the plane of the surface and relative to the shape; and applying a solution comprising a plurality of molecular shapes to the patterned surface of the substrate, the molecular shapes being generated using a polynucleotide platform, each of the molecular shapes having: a binding face that has high binding affinity for the one or more binding sites; a non-binding face that has low binding affinity for the one or more binding sites; a shape of the binding face matching to the shape of the one or more binding sites; and a second orientation direction defined relative to the shape of the molecular shapes, each of the molecular shapes having a higher binding affinity for the one or more binding sites with the second orientation direction aligned with the first orientation direction.

Each of the molecular shapes may include a fluorophore having a dipole rigidly oriented with respect to the second orientation direction, wherein the method further includes fabricating a photonic crystal cavity on the substrate, the one or more binding sites being located at one or more defined locations within the photonic crystal cavity.

The patterning may be performed using nanoimprint photolithography, microcontact printing, nanocontact printing, or dip-pen nanolithography.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, together with the specification, illustrate exemplary embodiments of the present invention, and, together with the description, serve to explain the principles of the present invention.

FIGS. 8A, 8B, and 8C depict the energy landscapes of idealized versions of various shapes at six different orientations of the shape with respect to the binding site (at 60° intervals).

FIGS. 9A and 9B are AFM and averaged AFM (of over 600 binding sites) images of DNA origami placement on arrays of disk-shaped (FIG. 9A) and shape-matched (FIG. 13B) binding sites according to one embodiment of the present invention.

FIGS. 9C and 9D depict fluorescence microscopy of TOTO®-3 intercalated into DNA origami placed arrays on disk-shaped (FIG. 9C) and shape-matched (FIG. 9D) sites (ex. 642 nm; em. 660 nm) according to one embodiment of the present invention.

FIGS. 9E and 9F depict the intensity (red dots) of 600 sites depicted in FIGS. 9C and 9D as a function of excitation polarization $\beta$, where the blue line is a best fit line.

FIG. 12 depicts further analysis of the orientation data shown in FIG. 10 and FIG. 11.

FIG. 15 depicts comparisons of different methods for aligning nanoscale devices.

FIGS. 19A through 19N are a schematic illustration of a process flow for fabricating PCC arrays according to one embodiment of the present invention.

FIG. 20 microscopy images of photonic crystal arrays according to some embodiments of the present invention.

FIG. 20A is a scanning electron microscopy (SEM) image of a section of the 13×6 PCC array described above, where the scale bar is 2 µm. The inset shows critical dimensions of different features of the PCC: a =256 nm, r/a=0.3, $r_1$/a=0.2, $r_2$/a=0.25, s=0.22a.

DETAILED DESCRIPTION

Figure 1:
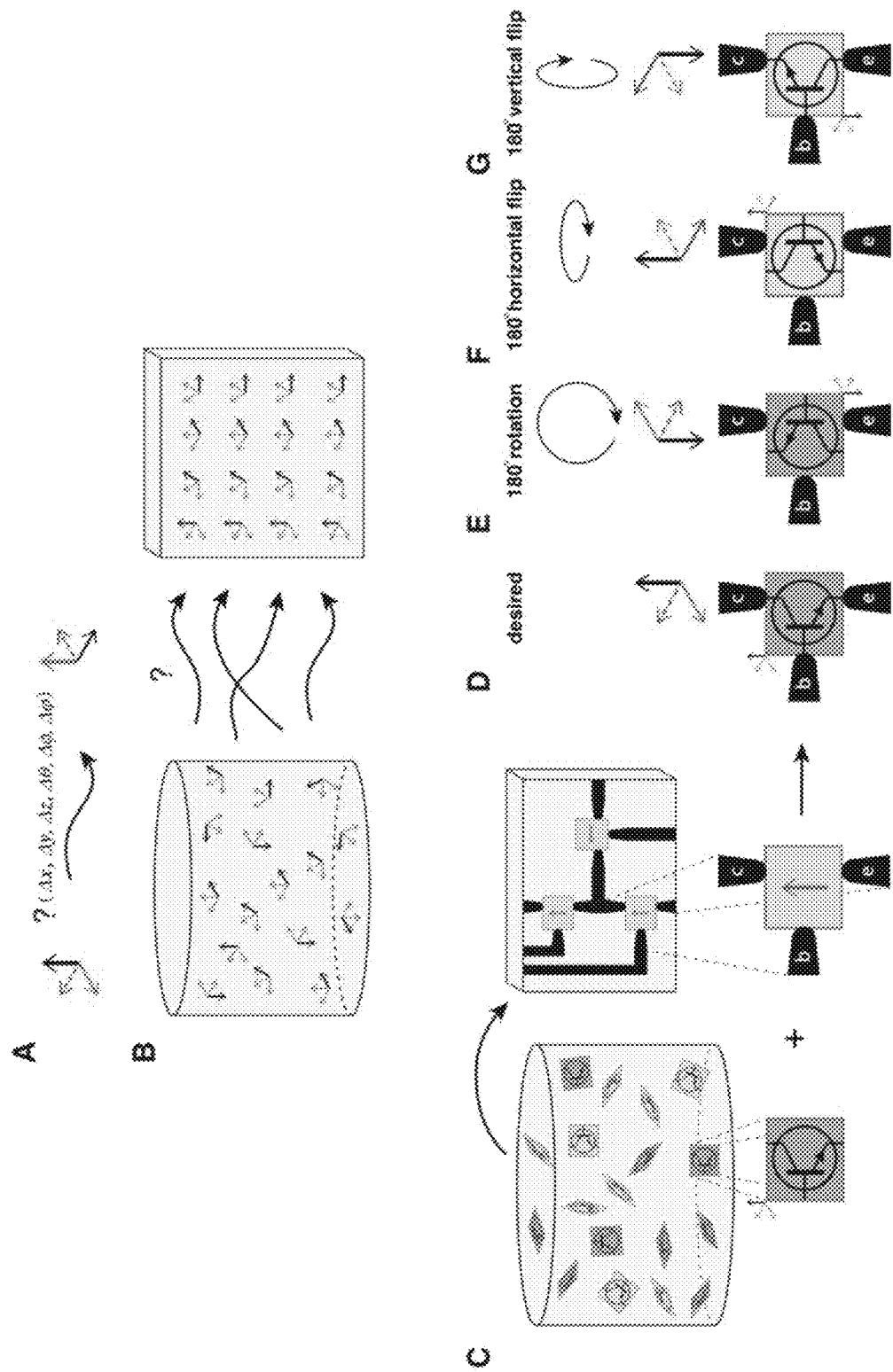
FIG. 1 illustrates problems associated with directed self-assembly of origami templated devices.

In the following detailed description, only certain exemplary embodiments of the present invention are shown and described, by way of illustration. As those skilled in the art would recognize, the invention may be embodied in many different forms and should not be construed as being limited to the embodiments set forth herein.

The sequential combination of solution-phase self-assembly (SPSA) and directed self-assembly (DSA) provides a general paradigm for the synthesis of nanoscale devices and their large-scale integration with control circuitry, microfluidics, or other conventionally-fabricated structures. Deoxyribonucleic acid (DNA) origami techniques have been shown to enable the solution-phase self-assembly creation of devices at sub-lithographic scales. An example DNA origami (see, e.g., Rothemund, Paul WK. "Folding DNA to create nanoscale shapes and patterns." Nature 440.7082 (2006): 297.) may incorporate up to two hundred nanoscale components, organized at a resolution of 3 nm to 5 nm, at precise positions and orientations (e.g., at orientations that can be precisely designed and controlled) with respect to the overall DNA origami molecule. Specific examples of nanoscale components that have been shown to be incorporated onto DNA origami molecules include carbon nanotubes, metal nanoparticles, fluorescent molecules, quantum dots, and conductive polymers.

Directed self-assembly (DSA) techniques generally use topographic or chemical patterning, fields, or flow to control the higher order structures of molecules and particles. While DSA is well developed for continuous block copolymer films, spherical nanoparticles, and linear nanostructures, DSA is less developed for DNA origami-templated devices for which shape and symmetry play a role in the function of the device and its integration with other devices.

Aspects of embodiments of the present invention relate to the directed assembly (or placement of) "molecular shapes" created using a polynucleotide platform (e.g., a general architecture for the generation of well-defined two-dimensional or three-dimensional shapes from polynucleotides) onto substrates. Polynucleotide platforms include but are not limited to scaffolded deoxyribonucleic acid (DNA) origami (Rothemund, Paul WK. "Folding DNA to create nanoscale shapes and patterns", Nature 440.7082 (2006): 297), scaffolded ribonucleic (RNA) origami (Torelli, Emanuela et al, "Isothermal folding of a light-up bio-orthogonal RNA origami nanoribbon", Scientific Reports 8 (2018): 6989), scaffolded hybrid DNA:RNA origami (Wang, Pengfei, et al. "RNA-DNA hybrid origami: folding of a long RNA single strand into complex nanostructures using short DNA helper strands", Chemical Communications 49 (2013) 5462-5464), scaffold-free DNA single-stranded tile (DNA brick) systems (Wei, Bryan, et al., "Complex shapes self-assembled from single-stranded DNA tiles", Nature 485 (2012):623-626 and Ke, Yonggang, et al., "Three-Dimensional Structures Self-Assembled from DNA Bricks", Science 338 (2012):1177-1183), scaffold-free multi-stranded DNA tile systems (Winfree, Erik, et al., "Design and self-assembly of two-dimensional DNA crystals", Nature 394 (1998) 539-44) or RNA tile systems (Chworos, Arkadiusz, et al., "Building programmable jigsaw puzzles with RNA." Science 306 (2004):2068-72), intramolecularly-folded single-stranded RNA (Geary, Cody, et al., "A single-stranded architecture for cotranscriptional folding of RNA nanostructures", Science 345 (2014) 799-804) or single-stranded DNA origami (Han, Dongran, et al., "Single-stranded DNA and RNA origami", Science 358 (2017): eaao2648). For the sake of clarity, aspects of embodiments of the present invention will be described herein primarily in the context of scaffolded DNA origami as a particular instance of a "molecular shape." However, embodiments of the present invention are not limited to scaffolded DNA origami. Instead, embodiments of the present invention include molecular shapes made using other polynucleotide platforms, such as the platforms listed above, where some examples of applications of embodiments of the present invention to other polynucleotide platforms are described in more detail below.

In particular, aspects of embodiments of the present invention relate to methods for controlling the absolute position and orientation of asymmetric DNA origami with respect to a reference frame of the substrate (e.g., a macroscopic reference frame). In other words, some aspects of embodiments of the present invention enable the reliable placement of DNA origami onto the surface of a substrate at positions and orientations specified by a design (e.g., the design of an engineered device).

Related work in DNA origami placement (DOP) has enabled some control over the position and orientation of DNA origami using lithographically patterned binding sites on the substrate (see, e.g., R. J. Kershner, L. D. Bozano, C. M. Micheel, A. M. Hung, A. R. Fornof, et al. Placement and orientation of individual DNA shapes on lithographically patterned surfaces. *Nat. Nanotechnol.*, 4(9):557-561, 2009, Erika Penzo, Risheng Wang, Matteo Palma, and Shalom J. Wind. Selective Placement of DNA Origami on Substrates Patterned by Nanoimprint Lithography. *J. Vac. Sci. Technol. B*, 29(6):06F205, 2011, and A. Gopinath and P. W. K. Rothemund. Optimized assembly and covalent coupling of single-molecule DNA origami nanoarrays. *ACS Nano*, 8(12):12030-12040, 2014.).

However, prior work with DNA origami placement has focused exclusively on binding sites that are equilateral triangles in shape, which can allow a planar, triangular DNA origami to attach in six different orientations: three rotations about an axis perpendicular to the substrate (spaced 120° apart) and two rotations about an axis parallel to the substrate (e.g., spaced 180° apart, in other words, flipped right-side up or up-side down). Thus, comparative DNA origami placement techniques using equilateral triangles does not enable absolute orientation of the DNA origami and its use is limited to devices with compatible symmetry, e.g. point-like devices, three-fold symmetric devices, or six-fold symmetric devices. Furthermore, prior work has been shown to allow DNA origami to be aligned within ±10° of a designed orientation (θ), which may not be sufficiently precise for many applications.

As a more specific example, FIG. 1 illustrates problems associated with directed self-assembly of origami templated devices. FIG. 1A depicts the mathematical problem of absolute orientation, where bold arrows show in-plane axes, dotted arrows point into page, and regular arrows point out. FIG. 1B depicts the physical problem of absolutely orienting solution-phase (blue) devices onto planar substrates (gray) so that each device has an arbitrary, user-specified (or designer-specified) orientation. In the example shown in FIG. 1B, the goal is for every device in the same column to have the same orientation, but for devices in different columns to have different orientations. Aspects of embodiments of the present invention relate to enabling the organized placement of such asymmetric (e.g., $C_1$ symmetric) molecules. FIG. 1C depicts an example of a problem encountered by using a DNA origami placement scheme to place an asymmetric device (a bipolar junction transistor) using high symmetry origami-rectangles. In this scheme, rectangles would attach to binding sites (shown in green), but the origami could bind to the surface in four different orientations (shown in FIGS. 1D, 1E, 1F, and 1G). Two of these orientations are right-side up (FIGS. 1D and 1E, shown in purple) and two of these orientations are up-side down (FIGS. 1F and 1G, shown in orange). In order for the circuit to function, electrodes c, e, and b of the bipolar junction transistor can only connect to the collector, emitter, and base of the bipolar junction transistor in a single (desired) orientation (the orientation shown in FIG. 1D). Because only one of the four binding orientations results in a functioning circuit, this lack of control results in exponentially low yield—if n different DNA origami devices all needed to be placed in the correct orientations for the overall apparatus to function and each DNA origami device bound to its site in the correct orientation with probability 0.25, then the probability of self-assembling a fully functional apparatus would be $0.25^n$. In the case of just three devices, as shown in FIG. 1C, only $0.25^3$ (or about 1.6%), of such self-assembled circuits would have all three DNA origami devices in their correct orientations.

Alignment of DNA origami using flow or field using induced dipoles would allow the same four orientations. Field alignment of origami with fixed dipoles could break the in-plane rotational symmetry, but would still allow the two orientations shown in FIGS. 1D and 1F, which are related by a horizontal flip. In addition, such global methods would not allow the simultaneous control of the orientation of all devices deposited during a particular step, if those devices were to have different orientations (e.g., referring to FIG. 1C, the binding sites with the upward pointing arrows versus the binding site with the leftward pointing arrow).

Accordingly, aspects of embodiments of the present invention relate to the precise, controlled placement of DNA origami onto the surfaces of substrates, which allows DNA origami to act as a bridge between the the length scale of features achievable through conventional lithographic techniques and sub-lithographic length scales achievable through the solution-phase and directed self-assembly techniques commonly used to synthesize DNA origami. Embodiments of the present invention also enable DNA origami to serve as a bridge between lithographically fabricated devices and biological molecules, such as for use in hybrid devices (e.g., combinations of biological and electronic or optical devices on a single substrate).

Figure 2:
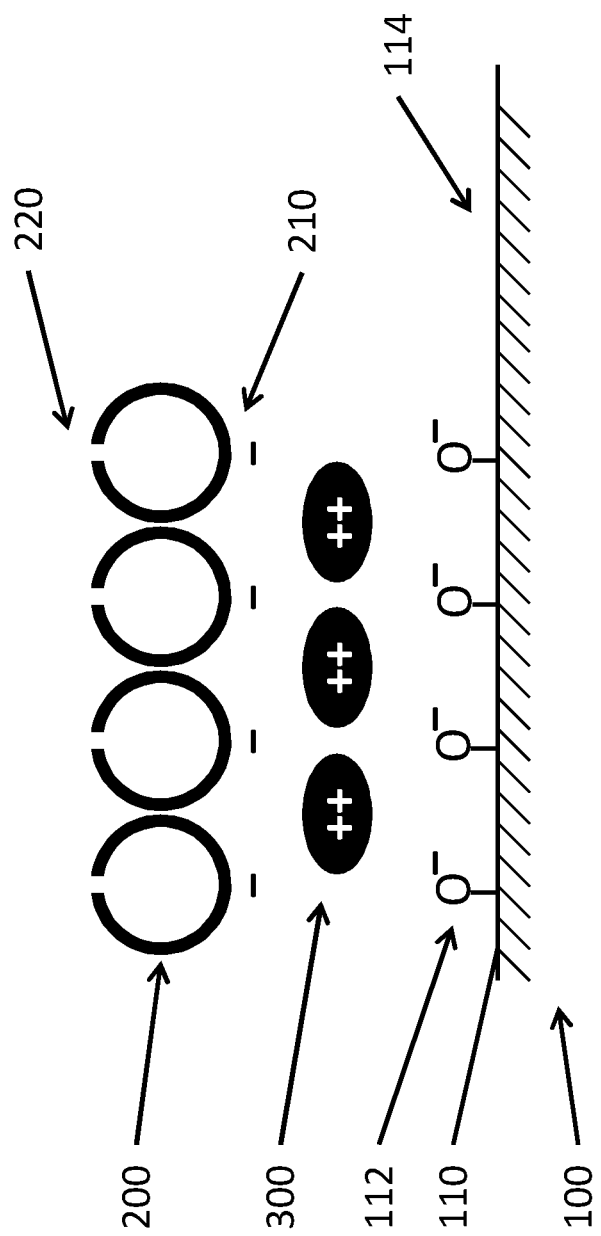
FIG. 2 is a schematic diagram of DNA origami placement.

FIG. 2 is a schematic diagram of DNA origami placement. Referring to FIG. 2, DNA origami placement can be performed on planar substrates 100 (such as $SiO_2$, quartz, silicon nitride [SiN] and diamond-like carbon) whose surface 110 can be differentiated into negatively-charged binding sites (depicted in the figures as green features) which bind negatively-charged DNA origami 200 strongly in the presence of bridging polyvalent cations (e.g., magnesium ions $Mg^{2+}$) 300, and a neutral background which binds origami weakly (depicted in the figures as gray backgrounds). In some embodiments of the present invention, electron-beam lithography is used to pattern binding sites (e.g., cure portions of a photoresist layer deposited onto the substrate), and the patterned binding sites (e.g., portions of a substrate where the photoresist has been removed in accordance with the curing) are made negative using silanols 112 which are ionized at the pH (8.3) of the origami binding buffer and the neutral background is a trimethylsilyl monolayer, generated via silanization of the surface 110 of the substrate 100. Nonbinding background portions 114 of the surface 110 of the substrate 100 may be unmodified (e.g., not silanized) and thereby bind to the origami more weakly than the binding sites. (In some embodiments, the nonbinding background portions may be modified to repel the DNA origami.) A planar DNA origami 200, as shown in FIG. 2 may be considered as having a first face 210 and a face surface 220.

The placement of DNA origami onto a substrate involves both three-dimensional diffusion of the DNA origami molecules to the surface of the substrate and two-dimensional diffusion of DNA origami that is weakly bound to the surface of the substrate along the plane of the surface. Observations of lateral jamming, binding of multiple origami to a single site, and reorientation of origami already bound to sites suggest that DOP is both non-equilibrium and non-Langmuir.

Aspects of embodiments of the present invention relate to two aspects: breaking up-down symmetry on a substrate surface such as unpatterned $SiO_2$ (e.g. differentiating between the pair of orientations in FIGS. 1D and 1E and the pair in FIGS. 1F and 1G, which differ by a rotation about an axis along the plane of the substrate); and breaking rotational symmetry in the context of DNA origami placement (e.g. differentiating between FIG. 1D and FIG. 1E, which differ by a rotation about an axis perpendicular to the substrate). While both aspects of symmetry breaking (up/down and rotational) are necessary to have full control over the absolute orientation of a molecule or device on a substrate, many uses of the present invention may only require one aspect of the present invention, for example breaking the up/down symmetry so that all molecules or devices land right-side up.

Figure 3:
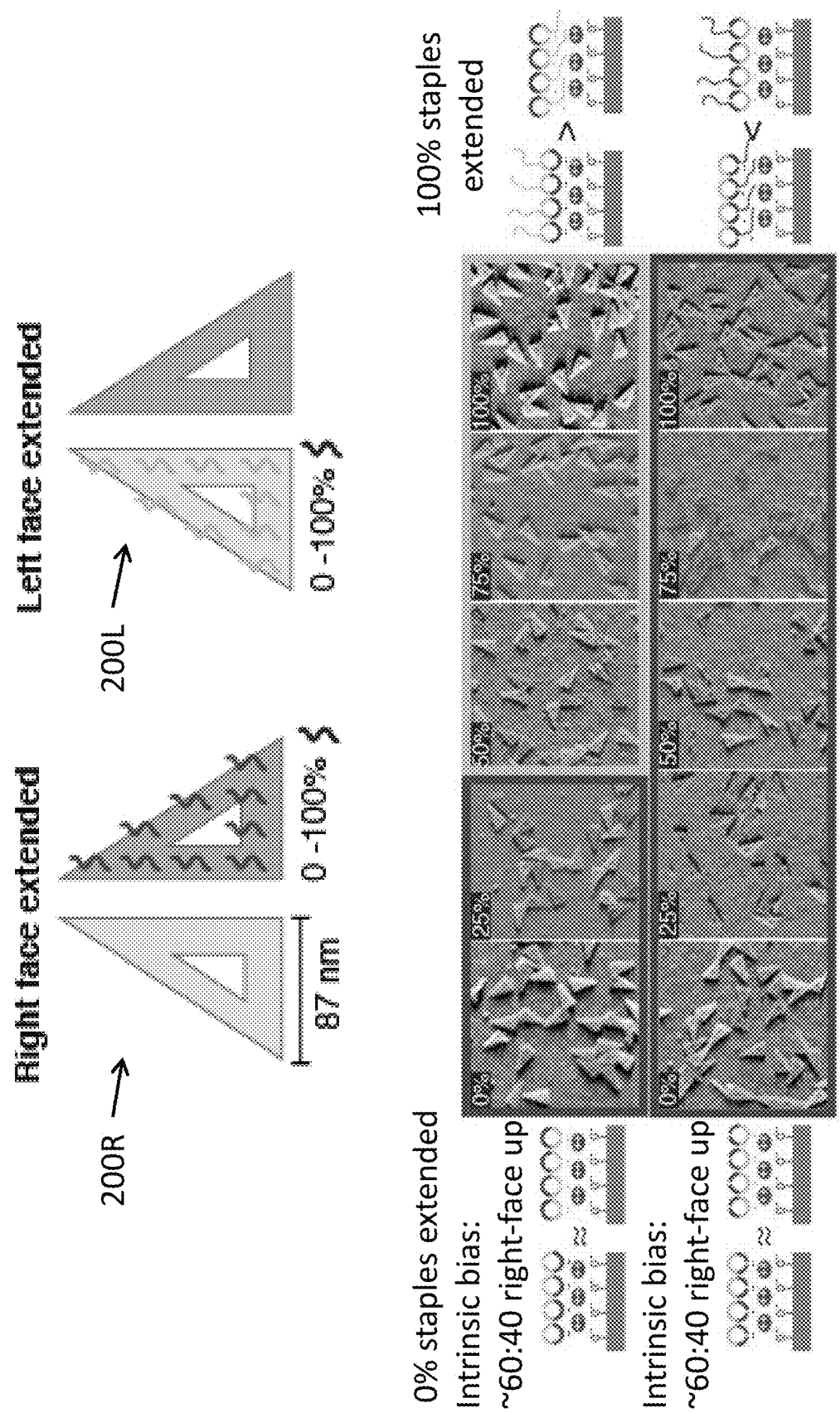
FIG. 3 illustrates two different versions of the right-triangle shaped DNA origami according to one embodiment of the present invention.

Accordingly, breaking up-down symmetry according to one aspect of embodiments of the present invention will be discussed first. FIG. 3 depicts one example of breaking up-down symmetry of DNA origami to control which side of asymmetric right triangle shaped DNA origami binds to the surface of the substrate. Each of the asymmetric right triangle DNA origami are synthesized through the solution phase self-assembly (SPSA) of two hundred short DNA staple strands with a long scaffold strand. Each of the asymmetric right triangle DNA origami has a "left" face (shown in orange) and a "right" face (shown in purple), which are distinguishable in atomic force microscopy (AFM) images of the origami deposited onto the planar surface of a substrate.

FIG. 3 illustrates two different versions of the right-triangle shaped DNA origami according to one embodiment of the present invention—one variant 200R in which the stapes on the right facing side of the triangle (shown in purple) are extended and one variant 200L in which the staples on the right facing left facing side of the triangle (shown in orange) using single stranded DNA (ssDNA) (in particular, a string of 20 thymine nucleotides or 20 nt, poly[T]) extending from the 5' ends of the staples.

Figure 4:
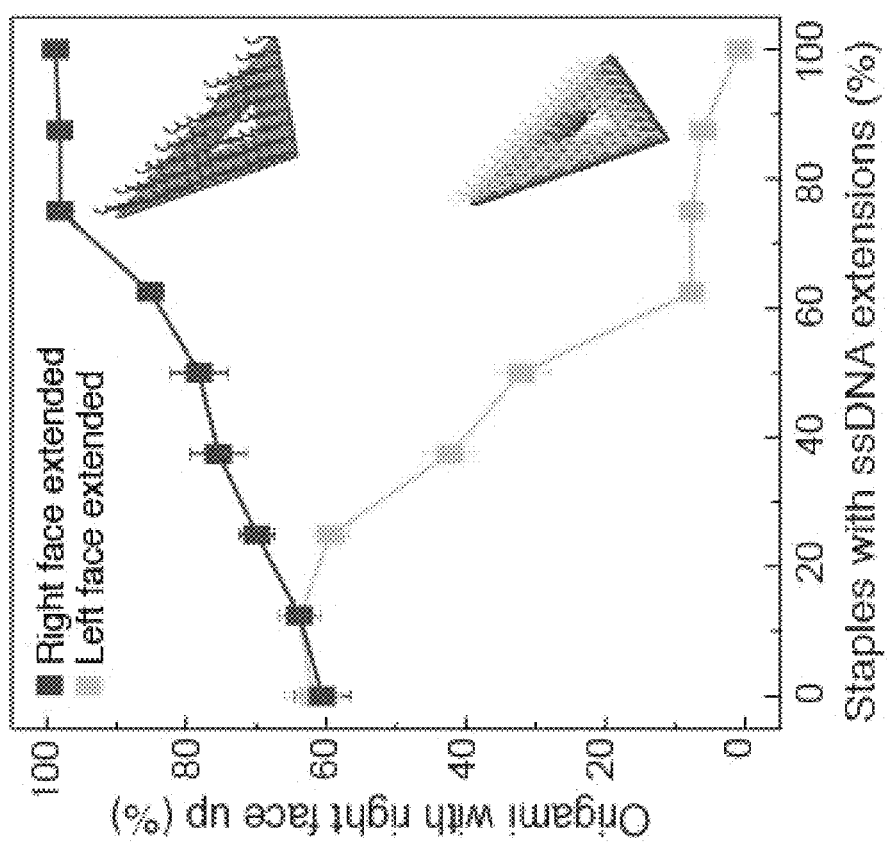
FIG. 4 summarizes the atomic force microscopy (AFM) data shown in FIG. 3.

To measure the effect of the extensions, five different sub-versions of the right-triangle shaped DNA origami were made, in which different percentages (0%, 25%, 50%, 75%, and 100%) of the staples included the extension. The percentages shown in FIG. 3 indicate the percentage of the 200 stapes of the DNA origami included the extension. The coloring of the DNA origami triangles in the atomic force microscopy (AFM) images identifies whether the origami has the right face (purple) facing up or the left face (orange) facing up. The colored outlines around the images indicate the bias (e.g., whether right face up or left face up is more prevalent in the particular image). AFM shows that extension-less (0%) right triangles exhibited a weak preference to bind unpatterned $SiO_2$ with their right face up (~60:40 right:left, FIG. 3). (This weak bias may be due to residual curvature due to imperfect twist correction of the right triangle designs.) FIG. 4 summarizes the atomic force microscopy (AFM) data shown in FIG. 3.

As seen in FIGS. 3 and 4, extensions on 100% of the staples caused nearly 100% bias on unpatterned $SiO_2$, with extensions facing up (away from the substrate). Extensions interfere with binding of negatively-charged phosphate groups to $Mg^{2+}$ ions 300 immobilized on ionized silanols 112 (green). Adding poly(A) ssDNA to make all extensions double-stranded and rigid abolished the bias. (This supports the idea that, on $SiO_2$, ssDNA extensions create bias by acting as entropic brushes which interfere with DNA-SiO2 binding.)

However, the symmetry-breaking effect of ssDNA extensions on $SiO_2$ does not necessarily generalize to other surfaces under the exact same conditions: on mica, where DNA-mica interactions are much stronger than DNA-$SiO_2$ interactions for the same $Mg^{2+}$ concentration, no bias was observed. To restore the symmetry breaking effects of ssDNA extensions when applying DNA origami to mica, the DNA-mica interactions must be weakened by for example changing (e.g. increasing) temperature or changing ionic conditions (e.g. decreasing $Mg^{2+}$ concentration, or adding a monovalent cation such as $Na^+$ as is taught in Woo, Sung-wook et al. "Self-assembly of two-dimensional DNA origami lattices using cation-controlled surface diffusion", Nature Communications 5 (2014) 5889). Further, on graphene, where π-π interactions between the unpaired bases and graphene are attractive, the bias is inverted (e.g., a DNA origami with single-stranded extensions is biased to bind with the side having the extensions facing the substrate).

Accordingly, aspects of embodiments of the present invention are directed to controlling which face of DNA origami binds to surfaces of substrates by breaking the up/down symmetry of the DNA origami, where the breaking of the up/down symmetry results in all or substantially all of the DNA origami to bind with the same face on the surface of the substrate. The degree to which an origami binds a substrate with a preference of one face over another is herein referred to as having a "bias" and therefore such "biased" molecules may be referred to herein as instances of Janus particles (particles whose faces have two or more distinct physical properties). This bias can be strong (nearly 100% of the origami bind via a single face to the surface), or it can be weak (slightly more than 50% of the origami bind via a single face to the surface). In various embodiments of the present invention, the up/down symmetry is broken by: designing one of the faces of the DNA origami to carry a molecule that binds more favorably to or with higher affinity for the substrate surface (and leaving the other face of the DNA origami unmodified with respect to the binding interaction); designing one of the faces of the DNA origami to carry a molecule that repels or binds less favorably to the substrate surface (and leaving the other face of the DNA origami unmodified with respect to the binding interaction); or modifying one face of the DNA origami to attract to the substrate surface and also modifying another face of the DNA origami to repel the substrate surface.

Accordingly, in the case of "two-dimensional" or planar DNA origami, there are four potential surfaces that can be modified in order to break the up-down symmetry of DNA origami binding to a substrate. These surfaces include two types of substrate surface and the two faces of the origami. By choosing the combination of the modification it is possible to break the up-down symmetry of the origami on arbitrary substrate materials. For the sake of convenience, the portion of the substrate surface that the DNA origami binds to will be referred to herein as the "binding site surface," or just "binding site" and the portion of the substrate to which the DNA origami binds weakly or is repelled will be referred to herein as the "nonbinding background." A surface of the DNA origami that is configured to attach to the binding site will be referred to as the "binding face" of the DNA origami, and a surface of the DNA origami that is configured to repel the binding site will be referred to as the "non-binding face." Both faces of the origami are assumed to repel or only weakly bind the nonbinding background of the substrate.

Embodiments of the present invention are not limited to use with two-dimensional or planar DNA origami. For example, DNA origami techniques may be used to make larger, more complex shapes such as three-dimensional boxes (e.g., using six DNA origami squares, attached at the edges to form a cube) and DNA origami may also be part of a larger structure (e.g., the DNA origami may be attached to other molecules, or even micron-sized particles using, for example, a DNA linker). However, in such circumstances, the DNA origami may still be used to attach the larger structure to a particular binding site on the substrate surface through interactions with the binding face of the DNA origami.

As noted above, the binding face of the DNA origami may be modified to increase attraction to the binding site, the non-binding face of the DNA origami can be modified to repel the binding site, and, in some instances, both the binding and the non-binding faces of the DNA origami may be modified to respectively attract and repel the binding site. The binding site may be modified to increase attraction to the binding face of the origami and/or repel the nonbinding face. The nonbinding background may be modified to repel both the binding and nonbinding faces of the origami. Thus in some embodiments, the chemistry of all four surfaces are chosen to work together to give optimal performance.

Accordingly, for embodiments using substrate materials which either have or can be treated to have thin surface oxide layers (e.g., but not limited to silicon dioxide, silicon, silicon nitride, silicon carbide, glass, quartz, gallium phosphide, indium oxide, indium tin oxide, and other materials) oxygen plasma treatment can be used to generate Si—OH or P—OH functional groups which are negatively charged at appropriate pH (e.g. typically pH 8.3 but origami can be used at least from pH 5-9), in order to create negatively-charged binding sites which work with high concentration $Mg^{2+}$ (typically 40 mM). The thin oxide layers on these same materials can be further silanized with negatively-charged carboxylate functionalities (via carboxysilanes) so that the concentration for $Mg^{2+}$ can be decreased to less than 10 mM. In such and similar embodiments, for which the binding sites have a negative charge, the binding face of the origami can be left unmodified (negatively charged). In general, the flatter the surface (lower root mean squared (RMS) roughness, with <1 nm roughness being preferred), the better the adhesion and the lower the $Mg^{2+}$ concentration which can be used.

In such embodiments (oxide/related surfaces with negatively charged binding sites) the nonbinding face of the origami can be modified with 20-base poly(T) single-stranded extensions (added to staples during synthesis of the DNA strands) if the $Mg^{2+}$ mediated binding of single-stranded DNA to the binding sites is not too strong. This approach works on silicon, silicon dioxide, and silicon nitride surfaces. Alternatively, a neutral polymer such as polyethylene glycol (PEG) can be attached to the nonbinding face via chemical coupling of a PEG-NHS (N-hydroxysuccinimide) to amine-modified staples (modified during synthesis). Alternatively, a neutral polymer such as poly(N-isopropylacrylamide) (PNIPAM) can be attached via growth by atom transfer radical polymerization from initiator-modified staples. In both cases (negatively charged DNA strands or neutral polymers) that the modifications may act as an entropic brush to prevent the nonbinding face from adhering to binding sites or the nonbinding background. Positively charged polymers such as poly-L-lysine may not be suitable for creation of nonbinding surfaces on origami, as such polycations cause DNA shapes to aggregate. However, poly-L-lysine with grafted PEG moieties (e.g., PLL-g-PEG) may be used to create a nonbinding surface of a DNA origami, as may other neutral polymers grafted to poly-L-lysine such as dextran (e.g., in the case of PLL-g-dextran). In such embodiments the positively charged poly-L-lysine serves as a linker to hold the neutral polymer on the negatively charged DNA origami, and the neutral polymer prevents aggregation of the origami.

To create a nonbinding background on such substrates (oxides/related surfaces), in some embodiments, hexamethyldisilazane (HMDS) is vapor-deposited to create a trimethyl-silyl (TMS) layer. This hydrophobic layer is effective for preventing unmodified origami binding, but can nonspecifically bind devices that the origami are designed to organize, for example proteins and small hydrophobic molecules. Thus the nonbinding surface on oxide-coated substrates can instead be created by solution silanization using large neutral polymers such as a silane-PEG (polyethylene glycol), or a silane coupled to poly(N-isopropylacrylamide) (PNIPAM). Alternatively, a silane coupled to a zwitterion such as sulfo-betaine (SBSi), or any number of common anti-fouling agents can be used. In embodiments where biological agents (proteins) are used as devices or in a detection application and nonspecific binding is problematic, a zwitterionic coating for the nonbinding background may be used.

In some embodiments, the substrate is a non-oxide substrate, wherein the binding sites are made negative via a method other than ionization of a silanol or silanization by a carboxylate. The binding site may still be a carboxylated, for example graphene surfaces can be carboxylated by treatment with pyrene-carboxylic acid. On molybdenum disulfide (or II-VI chalcogenide semiconductors like CdS, CdSe, TeSe) carboxylates may be introduced with a carboxy-diothiolane. In such embodiments, the binding face of the DNA origami can be left unmodified (negatively charged), or it can be modified with negatively charged small molecules (carboxylates) or negatively charged single-stranded extensions, or negatively charged polymers, or combinations thereof, so that the DNA origami can bind to the binding site through divalent cation mediated binding (e.g. $Mg^{2+}$). Depending on the substrate and choice of nonbinding background, the non-binding face of the DNA origami may be modified with negatively charged single-stranded DNAs, a neutral polymer coating, or zwitterionic coating as described above. The nonbinding background may be implemented by using the naked material if it is compatible with other surfaces in the system. For example, if graphene is used, and the nonbinding background is left to be naked graphene, then because naked graphene binds single-stranded DNA, the non-binding face of the origami cannot be implemented with single-stranded DNAs and must be implemented with a different modification such as a neutral polymer coating. Alternatively, if the nonbinding background is implemented using a pyrene-PEG (which will provide a neutral hydrophilic surface that does not bind single-stranded DNAs) then the nonbinding face of the origami can be implemented with single-stranded DNAs.

In some embodiments, the binding site may be modified by negatively-charged polymers, such as a carboxylated polyacrylamide. In such embodiments the binding face of the origami may be remain unmodified (if indirect binding via $Mg^{2+}$ is to be used) or may be modified with positively-charged amine groups on the staples (if direct binding between amines and the negatively charged polymer on binding sites is to be used). The nonbinding face may be unmodified (if amine groups are used on the binding face) or may be modified with single-stranded DNA extensions (if $Mg^{2+}$ is to be used), or in either case may be modified with neutral polymers. Depending on the substrate, the nonbinding background may be a naked (if naturally positively or neutrally charged) or modified with a neutral polymer or modified with a zwitterionic coating as above.

In some embodiments, the binding sites may be modified with positively-charged amine groups. On oxide materials or materials on which a thin layer of oxide can be formed (as described above) this can be accomplished with an aminosilane modification. On most materials (including graphene and mica) this may also be accomplished by treatment with a positively charged polymer such as poly-L-lysine (PLL) or poly-L-ornithine. On graphene this may be accomplished with an aminopyrene, and on molybdenum disulfide this may be accomplished with an amino dithiolane. In such embodiments, the binding face of the DNA origami can be left unmodified (negatively charged), or it can be modified with negatively charged small molecules (carboxylates) or negatively charged single-stranded extensions, or negatively charged polymers, or combinations thereof. The nonbinding face of the DNA origami may be modified with a neutral polymer coating as described above. Depending on the substrate, the nonbinding background may be a naked (if naturally negatively or neutrally charged) or modified with a neutral polymer or modified with a zwitterionic coating as above.

In some embodiments of the present invention, the binding site may be a catechol-binding material (e.g., a dopamine-binding material such as titanium (with a layer of oxide), titanium oxide, iron (with a layer of oxide) or iron oxide). In such embodiments the binding face of the origami is modified with a catechol (e.g., dopamine). The nonbinding face may be left unmodified, may have ssDNA extensions, or may be modified with a neutral polymer. Depending on the substrate, the nonbinding background may be an inherently non-catechol binding material, modified so that it does not bind a catechol, a naked (if it does not naturally bind DNA origami) or modified with a neutral polymer or modified with a zwitterionic coating as above.

In some embodiments of the present invention the binding site may be modified with thiol groups capable of forming covalent bonds. The binding face of the origami may be modified with thiols (for formation of a disulfide bridge), or with maleimide groups (for covalent bond formation via Michael's addition), or vinyl groups (for thioether formation). The nonbinding face of the DNA origami may be left unmodified (leaving just a phosphate backbone), or may be modified with negatively charged single-stranded DNAs or a neutral polymer coating as described above. Depending on the substrate, the nonbinding background may be naked, or modified with a neutral polymer or modified with a zwitterionic coating as above.

In general, any chemistry which is capable of forming a noncovalent or covalent bond, and which does not have strong electrostatic interaction, can be used to create the attraction between binding site and binding face of the origami. Examples include but are not limited to the streptavidin-biotin interaction (noncovalent) and alkyne-azide click reaction (covalent). By using such interactions instead of charged interactions, the nonbinding face of the origami can be to be used unmodified (or to be modified as desired or needed).

In some embodiments of the present invention the substrate surface at the binding site is a noble metal such as gold, silver, palladium or platinum. Thiols, poly(A) ssDNA, and DNA with a phosphorothioate backbone are known to bind strongly to gold and in combination these modifications of DNA can bind DNA even more strongly (Zhou, Wenhou et al., "Tandem Phosphorothioate Modifications for DNA Adsorption Strength and Polarity Control on Gold Nanoparticles", ACS Appl. Mater. Interfaces 6 (2014):14795-14800). In general, single stranded DNA binds gold and platinum, and it can do so with a particular sequence specificity (for example on gold, A>C>G>T as taught by Kimura-Suda, H. et al., "Base-Dependent Competitive Adsorption of Single-Stranded DNA on Gold", J. Am. Chem. Soc., 125 (2003): 9014-9015)

Accordingly in some embodiments involving naked noble metal binding sites such as clean and flat gold or platinum, the binding face of the DNA origami may be modified with thiol groups, a phosphorothioate backbone, adenine-rich single stranded DNA, or other single-stranded DNA (singly or in combination thereof) to attach to the metal surface of the binding site. Likewise, the non-binding face of the DNA origami may be left unmodified (phosphate backbone), modified with a repelling polymer coating (e.g., a weakly-gold-binding single-stranded DNA (polyT), double-stranded DNA, neutral polymers such as PEG, dextran or PNIPAM), or combinations thereof. In embodiments in which the nonbinding background of the substrate is also a noble metal, a thiolated neutral polymer such as thiol-PEG may be used to repel origami. Alternatively, a zwitterionic coating can be used to create a nonbinding background (e.g. via treatment with sulfobetaine-3-undecanethiol).

Single stranded DNAs are known to bind to the strongly hydrophobic (graphene or boron nitride) and moderately-to-strongly hydrophobic (molybdenum disulfide [$MoS_2$]) two dimensional and layered materials (e.g. materials which are a single layer of atoms, or a few layer of atoms). Accordingly, in some embodiments of the present invention, the binding site is naked graphene, boron nitride, molybdenum disulfide ($MoS_2$), or other similarly hydrophobic material, and the binding face of the origami is modified with single stranded DNAs. The particular single-stranded DNA sequence chosen will depend on the sequence-dependent affinity of the binding site material. For example, Varghese, N. et al ("Binding of DNA nucleobases and nucleosides with graphene." Chemphyschem: A European Journal of Chemical Physics and Physical Chemistry 10 (2009): 206-210) teaches that different DNA bases have differing preferences for graphene (G>A>T>C, where A's affinity is approximately equal to T). In such embodiments, the nonbinding face of the DNA origami may be left unmodified (phosphate backbone), or modified with a neutral polymer coating (e.g., PEG, PLL or PNIPAM), or combinations thereof to repel the surface of the substrate at the binding sites. The nonbinding background of the substrate may be created by coating with a neutral polymer, or zwitterionic material as described above, using a coupling method specific to the particular material (e.g. a pyrene-conjugated material in the case of graphene or dithiolanes in the case of molybdenum disulfide).

As above, in some embodiments, weak noncovalent interactions ($Mg^{2+}$ mediated electrostatic interactions to negatively charged binding sites), hydrophobic stacking interactions (single-stranded DNA extensions to graphene), are used. In general any relatively weak and cooperative molecular interaction can be used to create an attractive interaction between the binding face of the origami and the binding site of the surface. In such embodiments good performance relative to the quality of rotational orientation is expected (described in more detail below), as well as good performance relative to the quality of up-down orientation.

As above, in some embodiments, strong noncovalent interactions such as disulfide bridges, or amide bonds (formed between amines and carboxylates or NHS esters) are used. In general, any strong molecular interaction can be used to create an attractive interaction between the binding face of the origami and the binding site of the surface. In such embodiments somewhat lower performance is expected for rotational orientation, including the possibility that no rotational orientation is preferred. However high performance relative to the creation of a strong up-down bias is expected. In general higher performance relative to rotational orientation, may be achieved through any method which increases the reversibility of the strong interaction (e.g. heat or change of solvent/buffer conditions).

In embodiments for which single-stranded DNA is used for the interaction between the binding site and binding face of the origami, and in embodiments for which there is differing affinity of the binding site material (e.g. gold and graphene) for different single stranded sequences, then the sequence of the single-stranded DNA on the binding face can be used to tune the strength of the interaction, to optimize both rotational and up-down symmetry breaking. For example, if polyA binds too strongly to gold for good rotational orientation to be achieved, then polyT may be used instead. If polyG binds too strongly to graphene for good rotational orientation to be achieved then polyC may be used. Also, the length of the single-stranded extension may be varied to tune the strength of binding between the binding face and the binding site, with shorter length extensions (down to a single nucleotide) providing for weaker, more reversible binding.

In some embodiments, regardless of the chemistry used to make the origami binding face adhesive to the surface binding site, and regardless of the chemistry used to make the nonbinding face nonadhesive to the surface binding site, both the binding face and nonbinding face of the origami may be functionalized with a variety of chemical modifications, including but not limited to thiols, amines, biotins, maleimides, NHS esters, carboxylates, alkynes, azides, and hydroxyl groups which may be used to attach a variety of functional devices, both organic and inorganic, to either face of the origami, including but not limited to proteins (e.g., antibodies), small molecules (e.g., cholesterol), light emitters (e.g., quantum dots), or electronically active materials (e.g., carbon nanotubes).

In some embodiments, regardless of the chemistry used to make the origami binding face adhesive to the surface binding site, and regardless of the chemistry used to make the nonbinding face nonadhesive to the surface binding site, the origami may be modified with chemical linkers (on its binding face, on its edges, or from the nonbinding face in the case of suitably long linkers) which provide chemical functions that enable covalent linking of the origami to the surface after the directed self-assembly has occurred. For example, the origami may be modified with amine groups that can be chemically linked to carboxylate groups via amide bond forming. The advantage of such embodiments is that after such a covalent chemical cross-linking step, $Mg^{2+}$ or other cations can be completely removed from the system, the system can be stably moved to distilled water, or dried or moved under organic solvents and the origami on the surface will not fall off nor be denatured.

Figure 5:
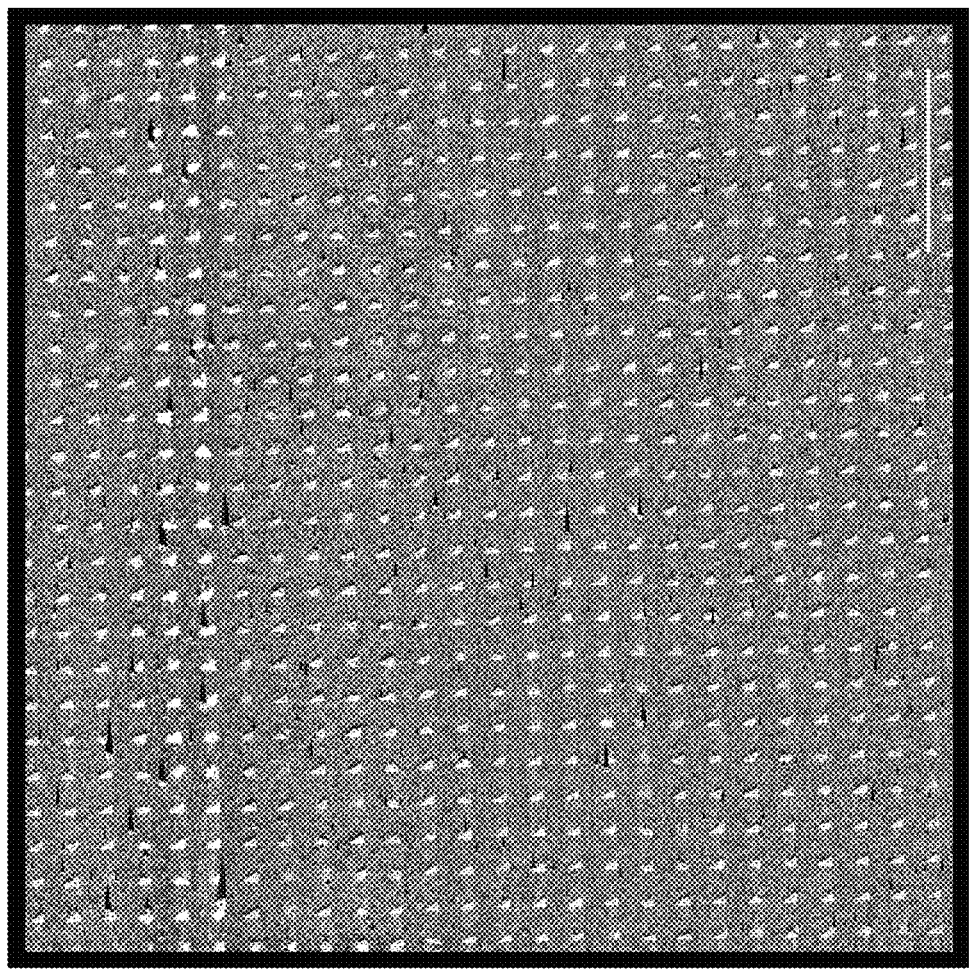
FIG. 5 is an AFM image of a substrate with right triangle DNA origami bound to right-triangle shaped binding sites.

Although the right triangle DNA origami shape shown above in FIGS. 3 and 4 is asymmetric, it does not reliably bind to right triangle shaped binding sites in the same rotational orientation. FIG. 5 is an atomic force microscopy (AFM) image of right triangle origami with its right-hand face 100% modified with 20 nucleotide poly(T) overhangs placed on right-handed binding sites. The placement conditions were 100 pM DNA origami, 10 mM Tris, 35 mM Mg2+, and pH 8.35 for a 60 minute incubation. The ovals shown in FIG. 5 identify examples of how binding events were scored. Red ovals identify single origami with roughly the desired orientation or orientation direction. Green ovals identify single origami with undesired orientations (or undesired orientation directions). Blue ovals identify empty binding sites (no origami). Purple ovals indicate double bindings or other unscored binding events. The orientation angles θ of each bound origami relative to its corresponding binding site (the red and green ovals) were measured for 437 sites out of 600 sites (about 73%), to the nearest multiple of 4.5°. The scale bar corresponds to 2 μm.

Figure 6:
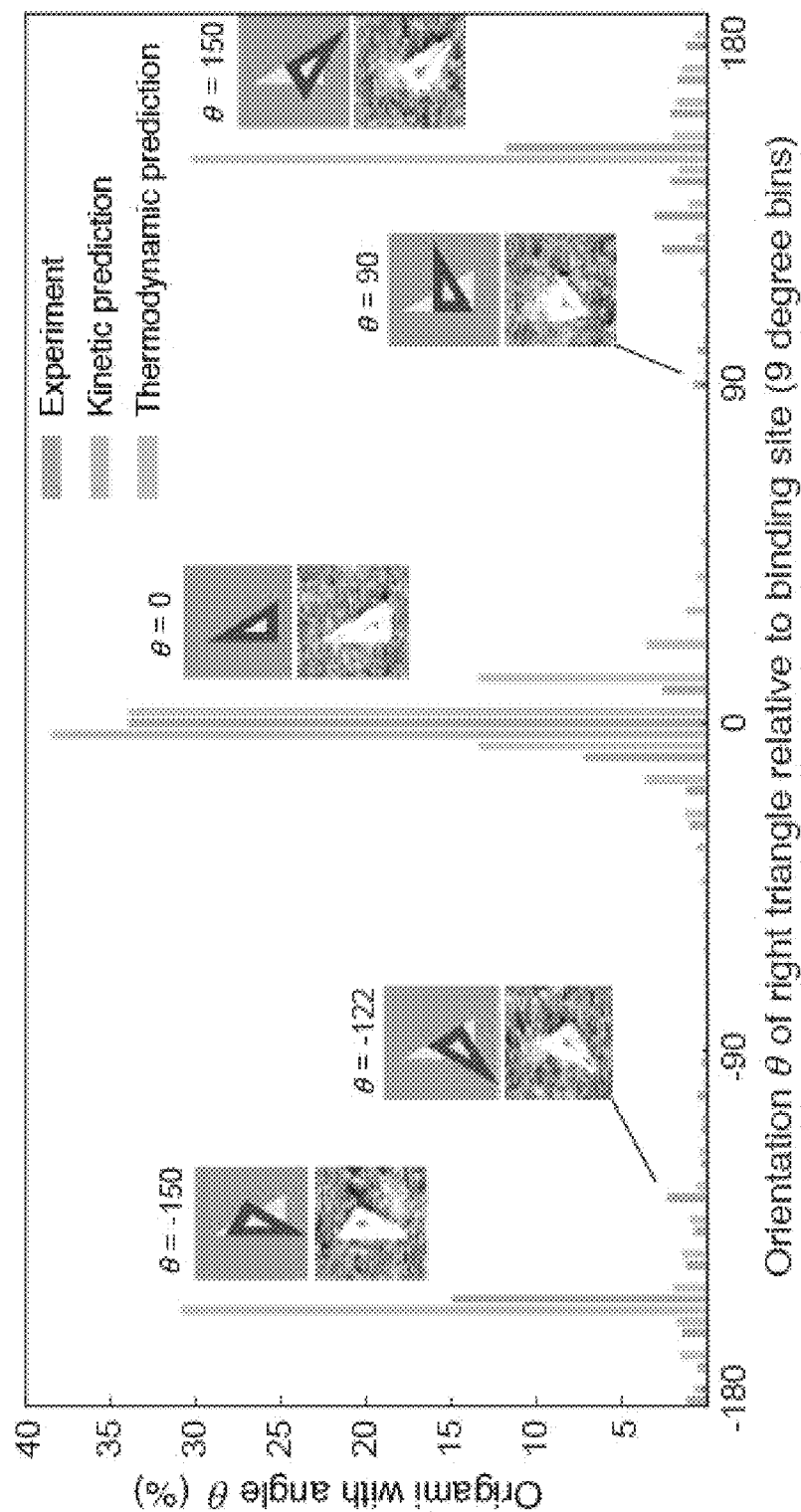
FIG. 6 presents AFM data (blue bars, N=437 sites) compared with kinetic (red) and thermodynamic (green) predictions for the percentage of right triangles bound at a given angle (within a 9° macrostate) on a shape-matched binding site.

FIG. 6 presents AFM data (blue bars, N=437 sites) compared with kinetic (red) and thermodynamic (green) predictions for the percentage of right triangles bound at a given angle (within a 9° macrostate or bin) on a shape-matched binding site. (As used herein, the term "shape-matched" or having a shape "matching" another shape refers to having substantially the same size and shape (e.g., the two shapes being substantially congruent). As shown in FIG. 6, only about 34% of the right triangle origami were bound with the desired alignment (θ=0°), which would result in low yield if used in fabrication processes for manufacturing, for example, a lab-on-a-chip using DNA origami placement techniques.

To further analyze the interactions between the DNA origami and the binding sites, the experimental results are compared with a kinetic model and an equilibrium model, with the assumption that the binding energy of a given state is linearly proportional to the area of overlap between the origami and binding site; θ=0°, with its total overlap of origami and binding site, has the highest possible binding energy. The state space was discretized in both x and y (1 nm increments), and θ (1° increments), encompassing more than 19 million states with positive overlap.

For kinetic predictions, shown with the red bars in FIG. 6, steepest ascent hill climbing was performed using all possible states as initial configurations. Neglecting variations in x and y, the state space has three basins of attraction whose maxima (θ=0, ±150°) corresponded with the three most common experimental states (shown by the blue bars in FIG. 6). Kinetic abundances predicted by measuring and normalizing basin volumes overestimated experimental abundances with relatively small factors (from 1.1× for θ=0° to 2.6× for θ=150°). Small changes to details of the model predicted the existence but not quantitative abundance of minority states (e.g. θ=−122° or θ=90°).

For thermodynamic predictions, shown in green bars in FIG. 6 expected equilibrium abundances were calculated from the partition function using an energy per unit area overlap derived by constraining the abundance at θ=0±4° to match experiment; thermodynamic abundances underestimated experimental abundances with large factors (from 5.5× for θ=150° to 7.3× for θ=−150°).

Therefore, the experimental data was most consistent with a strongly kinetically trapped regime in which origami enter the state space at random (when they collide with a binding site) and simply proceed to a local maxima in binding energy. Qualitatively, after the DNA origami reaches the surface of the substrate, it slides and/or rotates along the plane of the substrate to move into position with respect to a binding site. The energy landscape is depicted in FIG. 8A and is described in more detail below.

In order to overcome the problem of reliably orienting DNA origami onto correspondingly shaped binding sites, the DNA origami and the binding site should be shaped such that the DNA origami stays on its target binding site. The strong kinetic trapping exhibited by DNA origami placement constrains the energy landscapes which can robustly break rotational symmetry: the volume of a single basin of attraction must make up most of the state space and, in the best case, the landscape will have a unique global maximum.

Figures 7A, 7B:
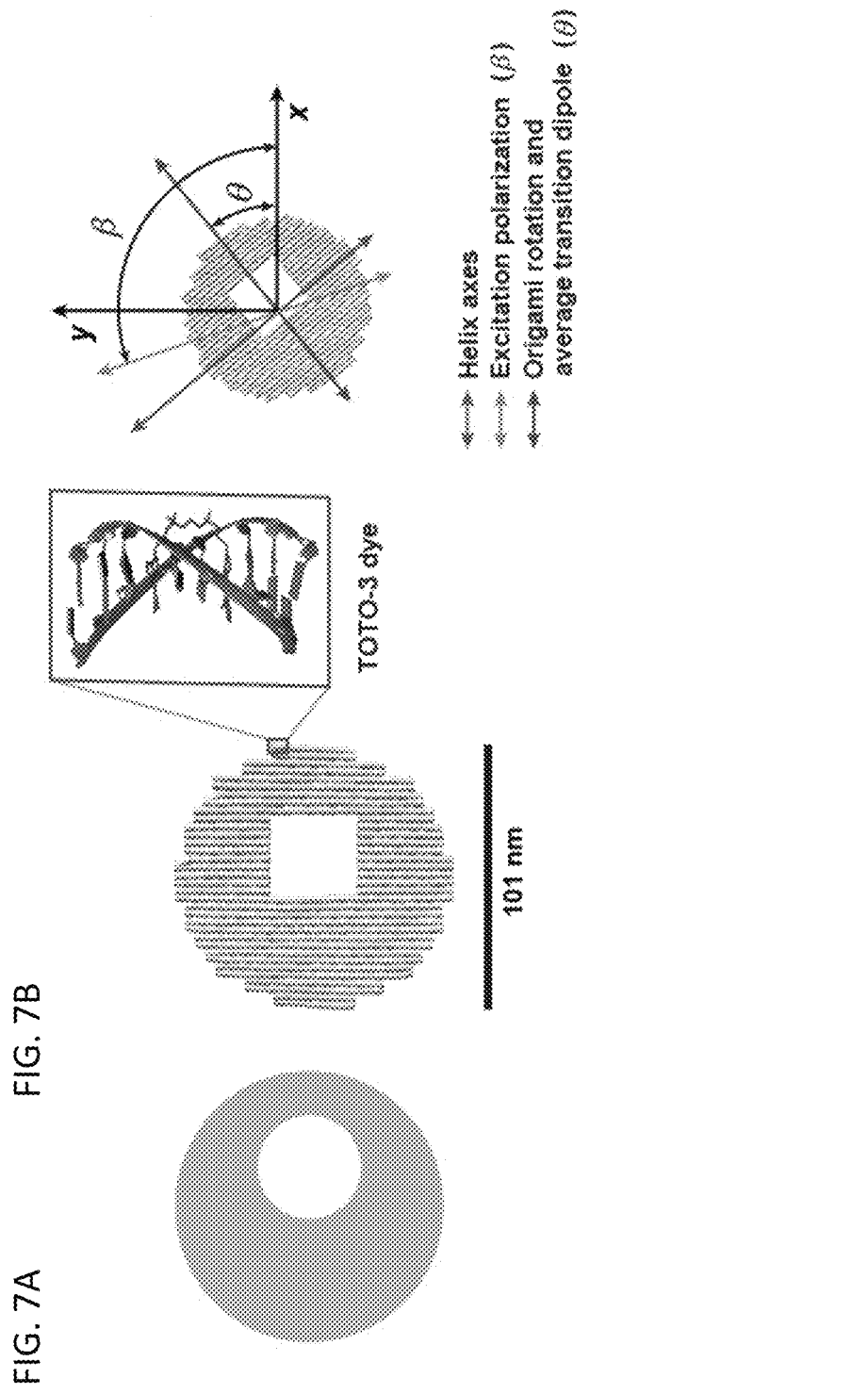
FIG. 7A is a depiction of a disk with offset hole shape.
FIG. 7B depicts the shape of a DNA origami according to one embodiment of the present invention having a shape approximating the disk with offset hole shape.

A shape satisfying this unique global maximum condition is a disk with an offset hole, as shown in ideal form in FIG. 7A. The disk with offset hole can be approximated by a DNA origami, as shown in FIG. 7B. For the sake of convenience, the shape will be considered to have an orientation direction along a line extending through the centers of the disk and the hole (shown as the red line in FIG. 7B). Accordingly, a binding site having an asymmetric shape (such as a shape satisfying the unique global maximum condition) can be considered to have an orientation direction (or a "first orientation direction") relative to the substrate (e.g., relative to an axis perpendicular to the substrate). Similarly, a DNA origami (or other molecular shape) having a shape corresponding to the shape of the binding site (having an asymmetric shape) can also be considered to have an orientation direction (or a "second orientation direction") with respect to an axis perpendicular to the substrate when that molecular shape has landed (e.g., is on) the substrate. In some embodiments, the DNA origami is stained with the TOTO®-3 dye. FIG. 7B depicts the rotation of the fluorescent dye TOTO®-3's absorption dipole along the length of a TOTO®-3 intercalated helix. Coordinate system shows relationships between helix axes (shown in blue), excitation polarization (β) and origami rotation (θ) with respect to the orientation direction.

As seen in FIG. 3B, in one embodiment of the present invention, the hole of the DNA origami is has a square shaped, sized such that it is circumscribed by a correspondingly shaped circular hole in the binding site. This particular embodiment was chosen because the particular architecture of DNA origami chosen was not compatible with a perfect approximation of a circular hole. However, embodiments of the present invention are not limited to the combination of a square shaped hole in the DNA origami and a substantially circularly shaped matching hole in the binding site. Instead, in various embodiments, the shape of the hole in the molecular shape may depend on the characteristics and constraints of the chosen polynucleotide platform, while substantially matching the shape of the hole in the binding site.

Figures 7C, 7D:
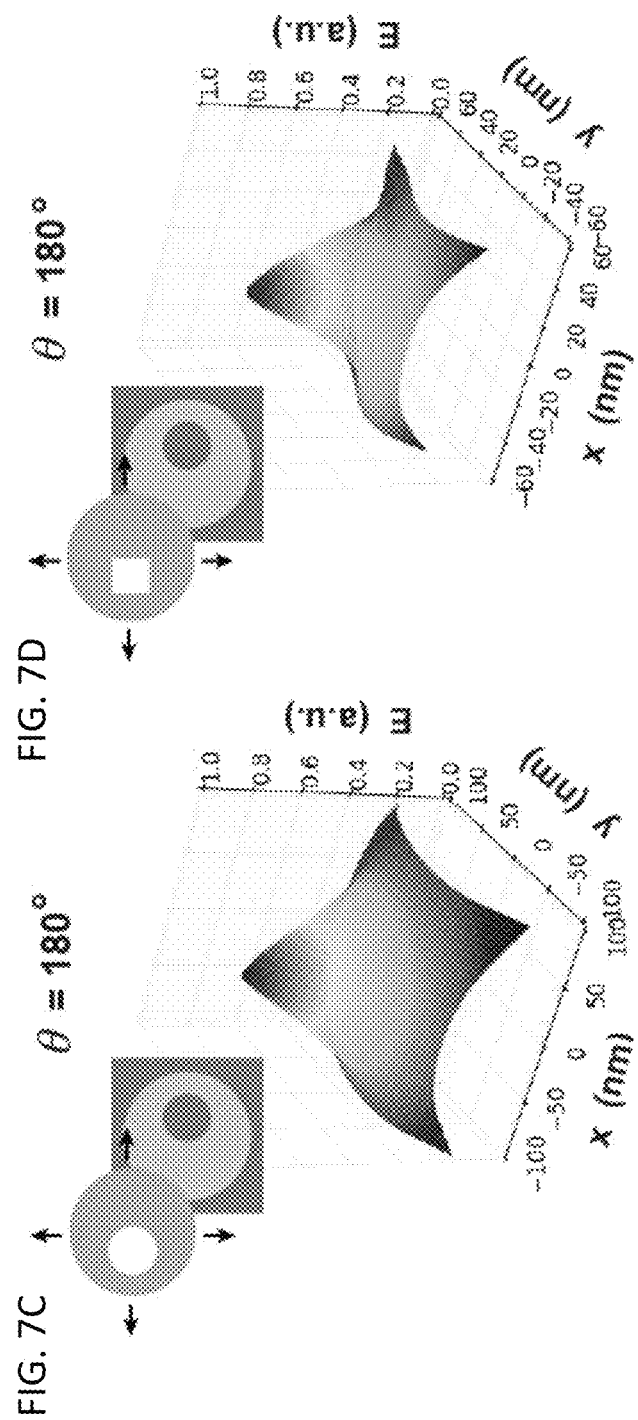
FIGS. 7C and 7D depict energy landscapes for different disks with holes and binding sites according to one embodiment of the present invention.

The performance of a shape with respect to absolute orientation can be studied by analyzing the energy landscape between the shape and a binding site, as a function of X-Y translation and rotation θ. FIG. 7C depicts the energy landscape for binding energy between an idealized disk with circular hole with a binding site shaped as a disk with a circular hole, where the binding site and the disk are oriented 180° with respect to one another (e.g., their orientation directions are pointing 180° apart). FIG. 7D depicts the energy landscape for binding energy between a disk with square hole with a binding site shaped as a disk with a circular hole, also where the binding site and the disk are oriented 180° with respect to one another. These diagrams provide an example for a fixed θ (180°) but a full analysis requires inspecting the energy landscape for all angles θ, either by using computation, or by using a mathematical proof. A molecular shape will bind a binding site with a unique orientation (e.g., with the orientation directions aligned and with the molecular shape translated along the plane of the substrate to overlap with the binding site) if there is a single maximum in the energy landscape.

With respect to mathematical proofs demonstrating unique orientation of a disk with a hole, proofs are easier for cases where the shape of the holes (for the shape and the binding site) is circular and their sizes match. However, as noted above, for practical reasons, it may be necessary to approximate a circular hole with a somewhat different, for example a similarly sized square. When mathematical proofs are difficult, the explicit energy landscape can be computed. The energy landscape in FIG. 7D demonstrates the relative insensitivity of the technique to the exact size/shape of the hole. The energy landscape for the disk with a square hole on a binding site with a circular hole is slightly deformed from the ideal shape-matched landscape, but it still exhibits a unique energy maximum, and will thus still provide a unique rotational orientation.

Figure 8B:
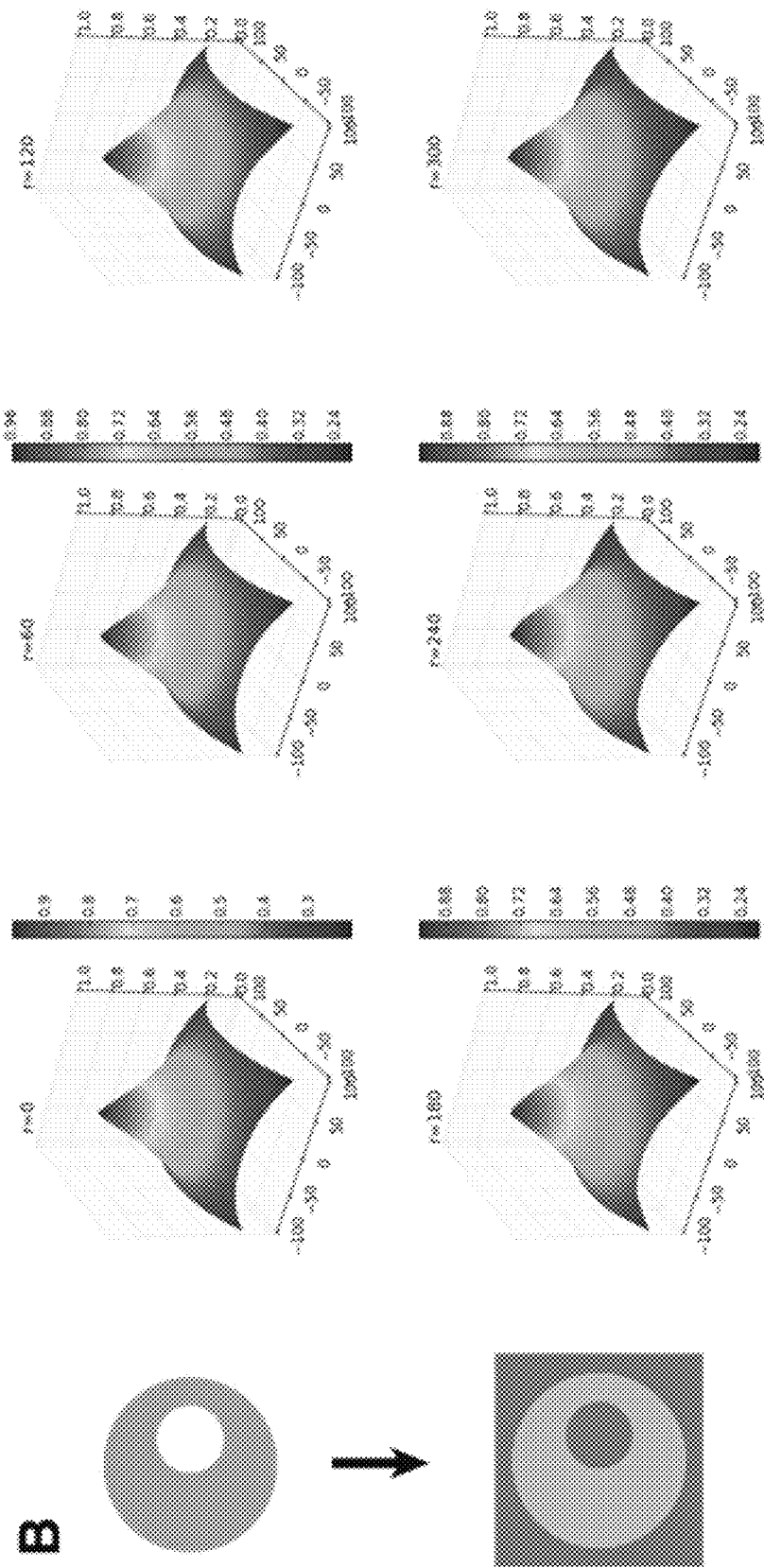
Figure 8C:
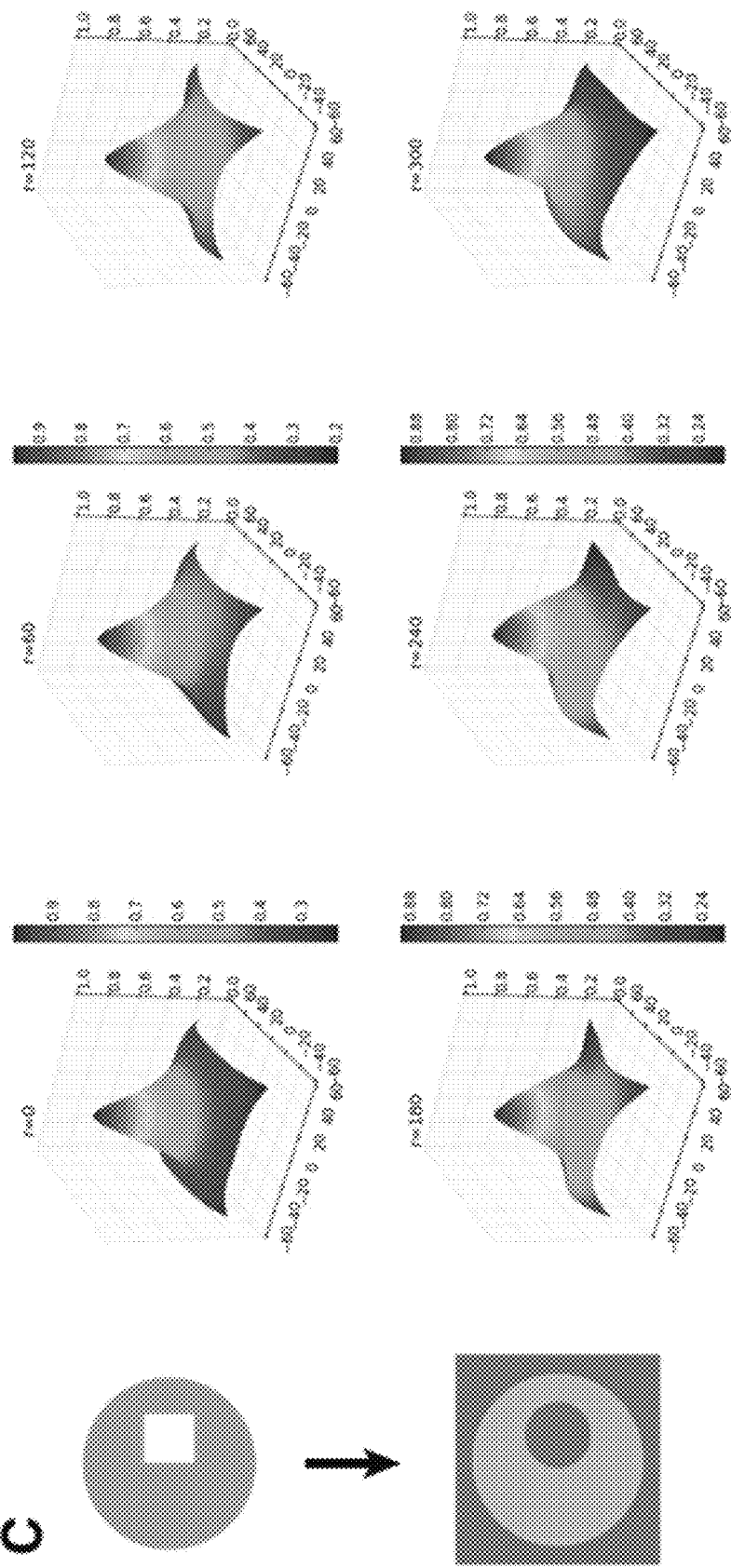

For purposes of illustration, FIGS. 8A, 8B, and 8C depict the energy landscapes of idealized versions of various shapes at six different fixed orientations (or orientation directions) of the shape with respect to the binding site (at 60° intervals). The colors in FIG. 8 run from high binding energy (red) to low (blue). While only six different orientations are illustrated, the energy landscape was computed and analyzed for all rotations in 60° increments. FIG. 8A depicts the energy landscapes for an asymmetric right triangle, where the energy landscape is rugged with multiple local maxima. Although the right triangle DNA origami has a hole, the binding site does not have a non-sticky region which matches the hole. Further simulations showed that adding a non-sticky region to match the hole (not shown) does not prevent the local maxima. Thus such an asymmetric right triangle cannot be used for absolute orientation (it cannot provide for a single unique orientation) of a molecular device coupled to a DNA origami.

FIG. 8B depicts the energy landscapes between a disk with an offset circular hole and a binding site having the shape of a disk with an offset circular hole. This corresponds to ideal disk with offset hole binding to an ideal disk with offset hole-shaped binding site; the landscape is a smooth inverted funnel with a single maximum. The binding site has a non-sticky region (or hole) which matches the hole in the origami; this offset hole breaks in plane rotational symmetry.

FIG. 8C depicts the energy landscapes between a disk with an offset square hole and a binding site having the shape of a disk with an offset circular hole. Because the shape of the hole in the experimental origami is a square, rather than a circle, the effect is that a single energy maxima is maintained but, at certain locations, the slope of the surface is slightly flattened compared to the energy landscapes shown in FIG. 8B.

Exact mathematical analysis of the energy landscape of the approximate disk with offset square hole was hindered by its complex jagged outline, so in the analysis of FIG. 8, the landscape was discretized as described above. Like its idealized counterpart, the DNA origami disk with offset hole has a unique global maximum in its energy landscape, although the square-shaped hole slightly flattens the landscape in some regions (compare FIGS. 7C, 7D, 8B, and 8C). Thus this set of six different fixed orientations (or orientation directions) further demonstrates that an approximate version of the disk with an off-center hole can yield good performance for orientation. Full analysis of the energy landscape over all angles from −180° to +180° (not shown) yields the same single maximum.

For the disk with the off-center hole, one can ask whether other deviations from the ideal shape will affect its performance in providing a unique orientation. Deviations from the idea shape might occur for the shape (because of an imperfect approximation by design, or due to experimental folding errors) or in the binding site (because of imperfect nanofabrication). In general, the shape is relatively insensitive to small changes in the shape or the binding site, and the relative size of the shape and the binding site can differ by a few percent, and good performance can still be achieved. However, if the binding site is much larger than the origami, then multiple origami can fit on and bind to the same binding site, which for many applications would be a serious defect.

The disk with the off-center hole shape is described in two papers, one theoretical paper (Xiong, Xioaorong, et al., "Geometric binding site design for surface-tension driven self-assembly", Proceedings of the IEEE Conference on Robotics and Automation, 2004, DOI: 10.1109/RO-BOT.2004.1307978) and one experimental paper (Liang, Sheng-Hsiung, et al., "Towards optimal designs for self-alignment in surface tension driven micro-assembly", 17$^{th}$ IEEE Conference on Micro Electro Mechanical Systems, 2004, DOI: 10.1109/MEMS.2004.1290509). The theoretical paper Xiong et al teaches a variety of facts concerning optimal radius for the off-center hole relative to the radius of the disk. The experimental paper Liang et al teaches fabrication millimeter-scale (1 millimeter) shapes from a silicon wafer, and teaches the construction of 1-millimeter binding sites from gold patches on silicon dioxide. In this experimental paper, millimeter scale parts were placed manually (by hand) onto binding sites, with tweezers. Neither of these papers teaches how to create a molecular implementation of the disk with an off-center hole (by creating a 100 nanometer DNA origami), nor how to break up-down symmetry which is necessary for absolute orientation, nor how to create 100-nanometer scale binding sites with appropriate binding chemistry for the DNA origami of the appropriate shape, nor how to exploit this for the purpose of creating actual devices. In contrast, aspects of embodiments of the present invention relate to how, given a particular theoretical shape, to implement this shape as a molecule using DNA, how to control this shape to land on a surface with the correct face of the molecule facing up, how to create a binding site on the surface with appropriate chemistry that matches the theoretical shape, and how to exploit this ability to create, for example, nanophotonics structures wherein the orientation of molecular light emitters is critical to device performance.

Accordingly, the present invention generalizes to other theoretical shapes, besides disks with offset circular holes, that can be used to accomplish unique orientation. For example, part of a "yin-yang" shape can be used. Consider the bent teardrop shape which comprises one half of yin-yang. A disk with a bent teardrop shape cut into its center can also provide for a unique energy minimum, as is taught in the theoretical paper Gopinath, Ashwin, et al., ("Progressive Alignment of Shapes", Proceedings of the 28$^{th}$ Canadian Conference on Computational Geometry, 2016, the entire disclosure of which is incorporated by reference herein). Thus, absolute orientation control in accordance with embodiments of the present invention can be achieved using given any theoretical shape which has a unique energy maximum in its binding energy landscape that can be rendered into a real molecular shape using a suitable polynucleotide platform and that can be constructed via lithography to pattern a suitable binding site.

Accordingly, the existence of multiple different theoretical shapes capable of generating absolute orientation means that the method can be used to position and orient more than one type of molecular device, either simultaneously in a single step of directed self-assembly wherein two or more different molecular shapes bearing different devices (or device attachment linkers) are simultaneously applied to a substrate, or through multiple steps of self-assembly wherein two or more different molecular shapes bearing different devices are applied to a substrate sequentially.

The up/down and rotational symmetry breaking in accordance with embodiments of the present invention is presented herein in the context of relatively rigid two-dimensional shapes. However, embodiments of the present invention are not limited thereto, and other embodiments of the present invention will allow the positioning and orientation of more complex shapes with respect to a substrate, either multicomponent shapes with reconfigurable geometry, or three-dimensional shapes which have been explored extensively in the literature of polynucleotide platforms. In such embodiments of the present invention, one component, part, or face of a more complex shape acts as a binding face that will break up/down symmetry, and, if desired, that binding face will be suitably asymmetric so that it can break rotational symmetry.

Experimental demonstration of the orientation of DNA molecular disks with an off-center hole is presented in FIG. 9. FIGS. 9A and 9B are AFM and averaged AFM (of over 600 binding sites) images of DNA origami placement on arrays of disk-shaped (FIG. 9A) and shape-matched (FIG. 9B) binding sites according to one embodiment of the present invention. As shown in FIG. 9A, the averaged AFM image is blurry and shows a hole roughly in the center of the disk, indicating random orientation of the DNA origami on the surface. In contrast, as shown in FIG. 9B, the image is sharper and the hole is offset to the right (e.g., the orientation of the DNA origami is pointing to the right side of the page), thereby confirming unique alignment of the DNA origami and demonstrating that the disk with offset hole shape of the DNA origami and of the binding site is able to achieve a high level of control over the orientation of the DNA origami when it is placed onto the substrate. By fitting the disk with offset hole shape to AFM of DNA origami having the disk with offset hole shape on shape-matched binding sites, the alignment was found to vary by ±6.7° (±1 SD). This variability includes both real variability due to fabrication error or imperfect assembly, and spurious variability due to the fitting of a model shape to poorly resolved origami; the latter error being more difficult to estimate.

In order to demonstrate an application of embodiments of the present invention and to improve measurements of alignment precision, DNA origami intercalated post-DOP with the fluorescent dye TOTO®-3 were imaged (see FIGS. 9C to 9F and FIGS. 10 and 11). This was done to demonstrate that, in addition to organizing DNA origami, embodiments of the present invention can impact orientation control over molecules (or more generally any nanostructure) that is rigidly bound to the DNA origami.

Two 600-binding site arrays of DNA origami having a disk with offset hole shape were created, one of the arrays (the control) had disk-shaped binding sites (no offset hole) and the second array had shape-matched binding sites (the binding site had the shape of a disk with an offset hole). Emission intensity for excitation polarization angle β was measured in 10° steps (sampling each β twice by rotating the stage from 0° to 350°) and fit the emission to derive distributions for the origami orientation direction θ. The emission peaks for polarized light having polarization angle β perpendicular to the helix axes was coincident with the origami orientation direction θ.

FIGS. 9C and 9D depict fluorescence microscopy of TOTO®-3 intercalated into DNA origami placed arrays on disk-shaped (FIG. 9C) and shape-matched (FIG. 9D) sites (ex. 642 nm; em. 660 nm) according to one embodiment of the present invention. In the left side images, the fluorophores were excited with horizontally polarized light (as indicated by the double-headed green arrow), and in the right side images the fluorophores were excited with vertically polarized light (as indicated by the double-headed green arrow).

Figure 10:
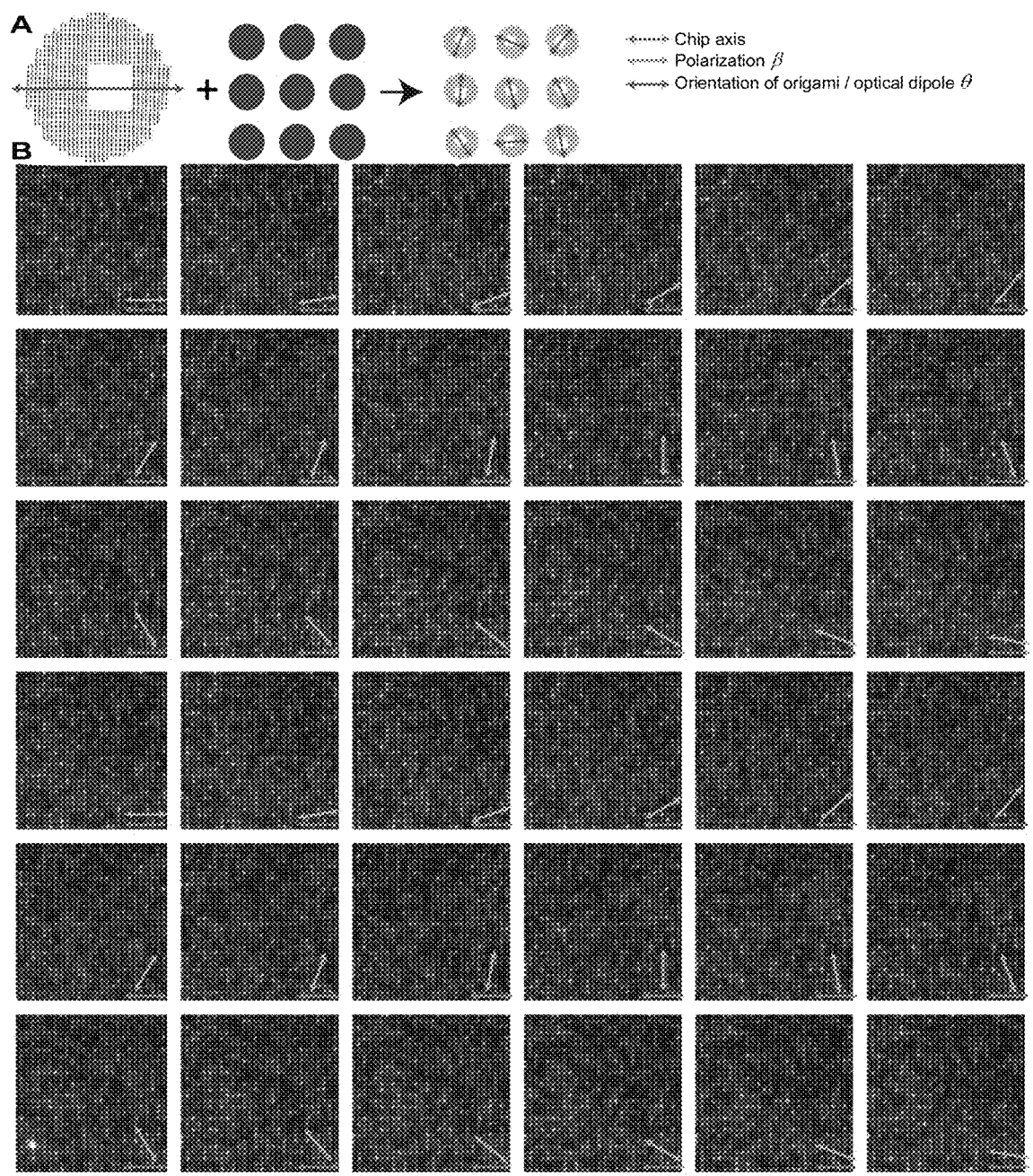
FIG. 10 depicts schematic and raw fluorescence data for disk with offset hole DNA origami placed on a 1 µm period square array with 105 nm diameter disk-shaped binding sites.

In the case of a disk shaped binding site, as shown in FIG. 9C, the DNA origami had random polarizations (as indicated by the red double-headed arrows) in both cases and, accordingly, random ones of the DNA origami emitted light in response to the horizontally and/or vertically polarized light. FIG. 10 depicts schematic and raw fluorescence data for disk with offset hole DNA origami placed on a 1 μm period square array with 105 nm diameter disk-shaped binding sites. FIG. 10A is a schematic illustration showing that DNA origami having the shape of disks with offset holes will bind to disk-shaped binding sites with random orientations and the excitation dipoles of intercalated TOTO®-3 fluorophores will therefore be uncontrolled. FIG. 10B shows 36 images where the rotation of excitation light polarization (green) relative to the array axis (blue) differs by 10° increments. Variations in the intensities of the light emitted by the DNA origami are uncorrelated, thereby indicating the random orientations of the DNA origami on the surface.

Figure 11:
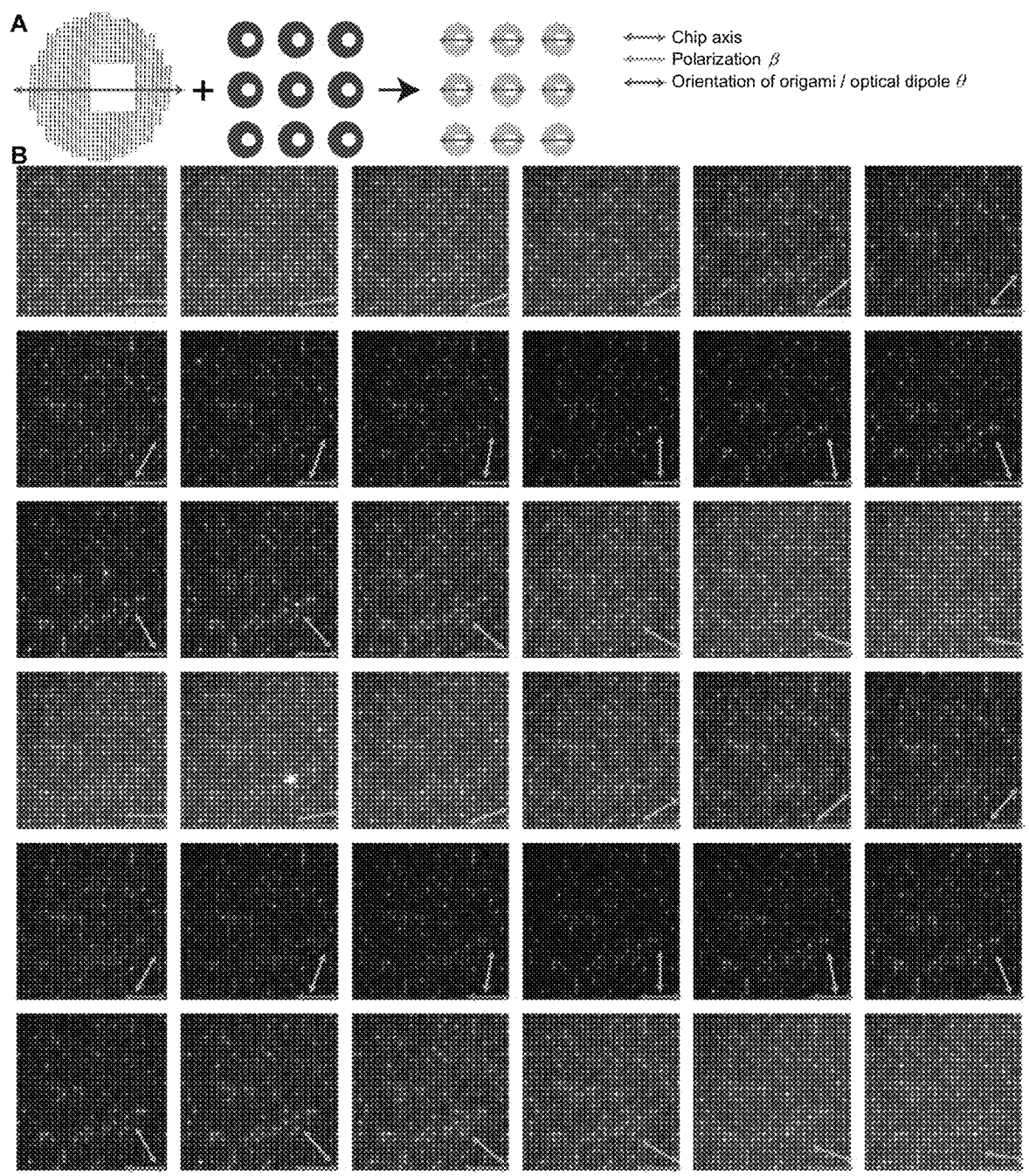
FIG. 11 depicts schematic and raw fluorescence data for disk with offset hole DNA origami placed on a 1 µm period square array of shape-matched binding sites according to one embodiment of the present invention.

On the other hand, in the case of the disk with offset hole shaped binding site, as shown in FIG. 9D, the binding sites oriented the DNA origami in a consistent direction (along the horizontal direction, (as indicated by the red double-headed arrows). Therefore, the DNA origami emitted light at higher intensity in response to the horizontally polarized light (on the left side of FIG. 9D) than in response to the vertically polarized light (on the right side of FIG. 9D), thereby indicating that the DNA origami were placed onto the surface in a consistent orientation direction aligned with the orientation direction of the binding sites. FIG. 11 depicts schematic and raw fluorescence data for disk with offset hole DNA origami placed on a 1 μm period square array of shape-matched binding sites according to one embodiment of the present invention. FIG. 11A is a schematic illustrating showing how the disk with offset hole DNA origami align to the shape-matched binding sites and, in turn, align the excitation dipoles of intercalated TOTO®-3 fluorophores. FIG. 11B shows 36 images where the rotation of excitation light polarization (green) relative to the array axis (blue) in 10° increments. Variations in intensity between these DNA origami are highly correlated, and the DNA origami are brightest when the polarization axis lines up with the array axis.

The strength of a molecular dipole μ excited by an electric field E along the direction of unit vector $\vec{e}$ =E/|E| is:

$$D(E)=|\mu \cdot \vec{e}|^2=|\mu|^2 \cdot \cos^2(\beta-\theta)$$

where β is the polarization of E, and θ is the in-plane dipole angle. According to the dipole approximation, emission is proportional to absorption, which is proportional to $|E|^2 D(E)$. Thus experimental intensity can be fit to:

$$I_o \cos'(\beta-\theta)+c$$

where $I_o$ is the maximum emission, and c is the background (camera noise, reflection). Emission from a collection of n molecular dipoles $\mu_k$ bound to an origami is proportional to $|E|^2 D_{net}$, where the net dipole strength is given by:

$$D_{net}(E) = \sum_{k=1}^{n} |\mu_k \cdot \vec{e}|^2$$

Figure 12B:
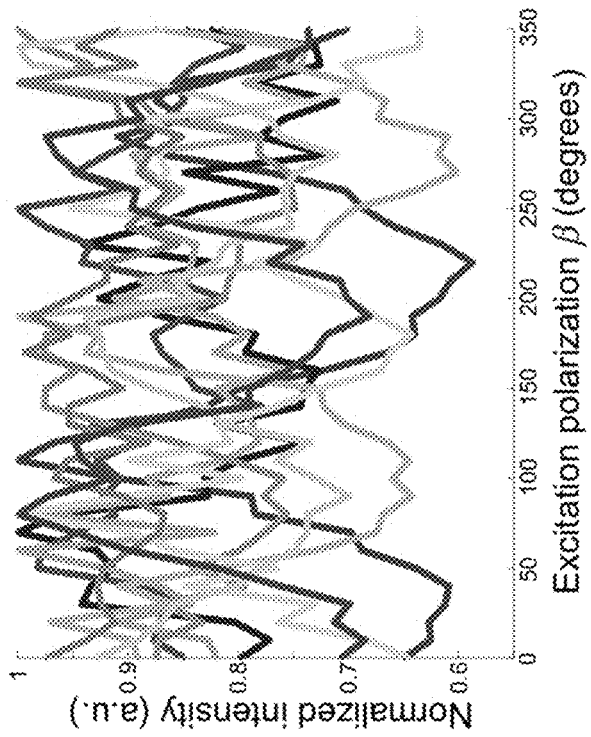
FIG. 12B is a graph depicting traces of fluorescence intensity from the ten binding sites highlighted in FIG. 12A as a function of the orientation of excitation polarization $\beta$.
Figure 12A:
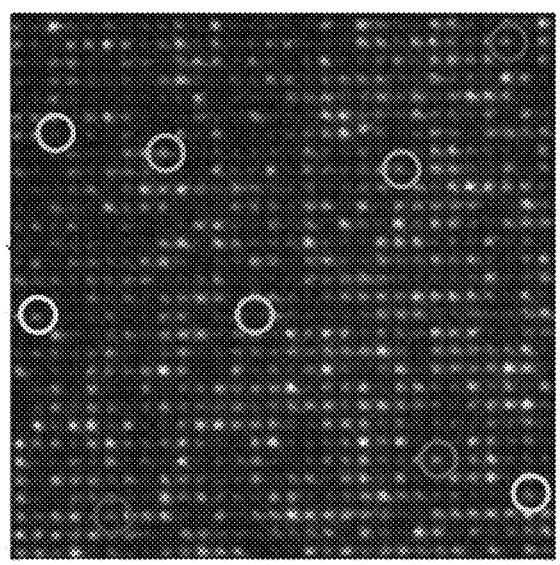
FIG. 12A is an AFM image of a subsection of data presented in FIG. 10, with TOTO®-3 labeled disk with offset hole shaped DNA origami bound to disk-shaped binding sites.

Thus the experimental intensity of n molecular dipoles with an anisotropic net in-plane dipole strength can be fit to the cost expression above: if $E_\parallel$ and θ are defined to lie along the direction of maximum net dipole strength, then $I_o$ is proportional to the difference $D_{net}(E_\parallel)-D_{net}(E_\perp)$ and c is the background plus a contribution proportional to $D_{net}(E_\perp)$, from the direction of smallest net dipole strength. As seen in FIG. 9E and FIGS. 12A and 12B (described in more detail below), emission from control sites individually fit this expression, but individual θ were uniformly distributed (see FIG. 12C, below), both confirming random origami orientation and ruling out polarization anisotropy in the setup of the experiments.

FIGS. 9E and 9F depict the intensity (red dots) of 600 sites depicted in FIGS. 9C and 9D as a function of excitation polarization β, where the blue line is a best fit line. Aggregate data for the control (disk shaped) binding sites could not be fit (see FIG. 9E). In contrast, aggregate data for shape-matched sites (FIG. 9F) fit θ=0° and fits to individual sites (see FIG. 12D, below) varying by ±3.2°, which is a current best measurement of alignment precision. These further confirm the control of the orientation direction of the DNA origami when bound to the surface of the substrate.

FIG. 12 depicts further analysis of the orientation data shown in FIG. 10 and FIG. 11. FIG. 12A is an AFM image of a subsection of data presented in FIG. 10, with TOTO®-3 labeled disk with offset hole shaped DNA origami bound to disk-shaped binding sites. Ten particular binding sites are highlighted with differently colored circles. FIG. 12B is a graph depicting traces of fluorescence intensity from the ten binding sites highlighted in FIG. 12A as a function of the orientation of excitation polarization β. All of the k=1 to 600 individual traces can be fit to the function $I_o \cos^2(\beta-\theta_k)+c$.

Figure 12D:
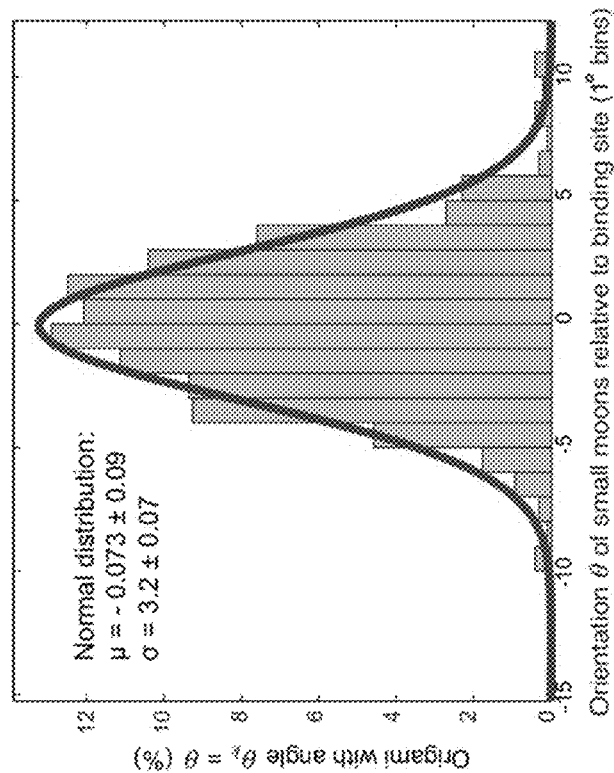
FIG. 12D is a histogram of orientation directions $\theta_k$ of disk with offset hole shaped DNA origami bound to shape-matched binding sites, aggregated into 1° bins from the data from FIG. 11.
Figure 12C:
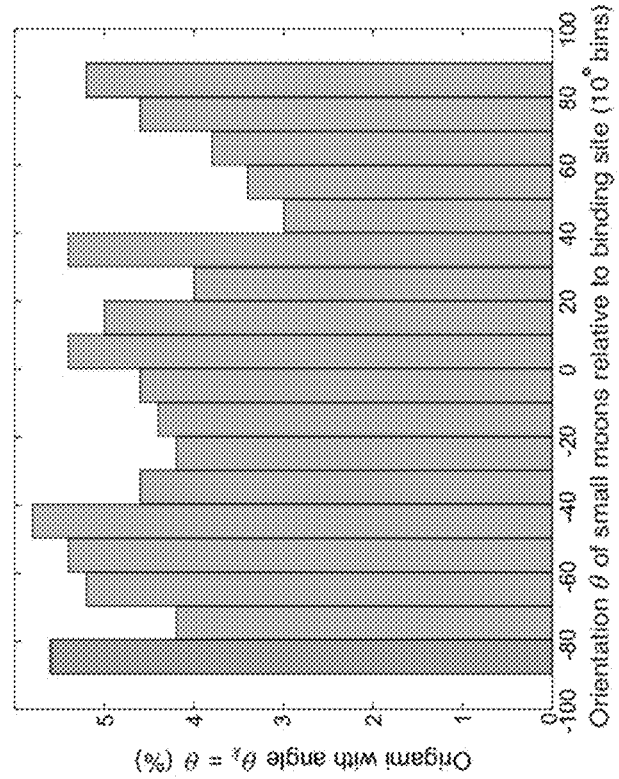
FIG. 12C is a histogram of orientation directions $\theta_k$ aggregated into 10° bins showing that the orientation directions $\theta_k$ of disk with offset hole shaped DNA origami are randomly distributed and therefore that the disk with offset hole shaped DNA origami exhibit no preferential orientation on disk-shaped binding sites.

FIG. 12C is a histogram of orientation directions $\theta_k$ aggregated into 10° bins showing that the orientation directions $\theta_k$ of disk with offset hole shaped DNA origami are randomly distributed and therefore that the disk with offset hole shaped DNA origami exhibit no preferential orientation on disk-shaped binding sites. The flat histogram further suggests that the experimental setup introduces no undesired anisotropy.

FIG. 12D is a histogram of orientation directions $\theta_k$ of disk with offset hole shaped DNA origami bound to shape-matched binding sites, aggregated into 1° bins from the data from FIG. 11. All of the shape-matched binding sites have the same orientation with respect to the substrate (e.g., global reference frame). As shown in FIG. 12D, the orientation directions $\theta_k$ cluster around 0° with a standard deviation of 3.2°, thereby showing that the orientation directions are highly correlated and substantially uniformly matched to the orientations of the binding sites. The red curve shows a best-fit line in accordance with a normal distribution.

As noted above, fluorescent dye (e.g., the carbocyanine dimer stain TOTO®-3) intercalation of DNA origami further enabled demonstration of control of orientation of the DNA origami on the surface of the substrate, prototyping of large-scale integration of orientation-dependent devices, and exploration of variables which can affect the quality of polarization-based devices. In one embodiment of the present invention, 66,980 DNA origami having the shape of a disk with an offset hole were placed onto a substrate surface, in one of two different orientations (the orientations being perpendicular to one another), which allowed the display of two different images based on the polarization angle β of the incident light. Bleed-through from one image to another was observed from origami with θ perpendicular to β. Through analysis of bleed-through for the data in FIG. 9F; after background subtraction, it was found that emission from origami oriented perpendicular to β was about 30% of that from origami oriented parallel to β. In interpreting the source of bleed-through, only the effect of dye alignment was considered, neglecting small polarization mixing effects of high numerical aperture on excitation polarization. In an ideal device, all dye molecules would align perfectly with $E_\parallel$: $D_{net}(E_\perp)$ and hence bleed-through would be zero. $D_{net}(E_\perp)$ combines contributions from both placement variabilities in θ with incoherence of dye angle relative to the origami. The contribution from placement variability is small, as bleed-through would be only 0.3% if the ±3.2° variability were the only source; ±39° variability would be required to explain the observed 30% bleed-through. The contribution from incoherent dye alignment within an origami is itself complex: it combines the deterministic rotation of φ by the DNA twist, random wobble from rotational diffusion (reduced here by intercalation and drying), potential alternative binding modes, and significant (~10.6°) back-and-forth bending of each helix axis in a DNA origami. Bleed-through may be simply explained by a combination of φ and helix bending, which are the most relevant variables for devices based on intercalators. Attributing all bleed-through to the dipole-helix angle yields φ=69° and adding helix bending increases the estimate of φ to 70°; both of which are consistent with φ previously measured for TOTO®-3 analogs. As with the addition of helix bending, adding other sources of dye alignment incoherence or excitation polarization mixing to the model would increase the estimate of φ; thus given the observed data, 69° is a lower bound for φ. On the other hand, even if φ=90° were achieved and all other sources of alignment incoherence removed, helix bending would still cause ~3.5% bleed-through, an unavoidable consequence of randomly intercalating dyes binding to both +10.6° and −10.6° bent helices. Devices with better-defined alignment relative to DNA origami, such as gold rods or single site-specific rigidly-linked chromophores, would exhibit much stronger polarization effects, limited only by the placement variability (i.e. 0.3% bleed-through might be attained).

Figure 13A:
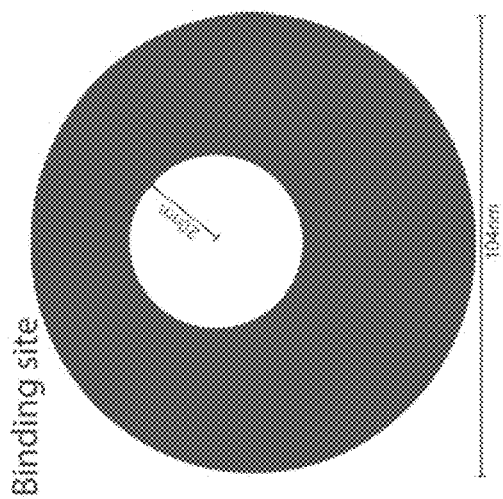
FIG. 13A depicts an example of a DNA origami having the shape of a disk with a square (or rectangular) offset hole according to one embodiment of the present invention.
Figure 13B:
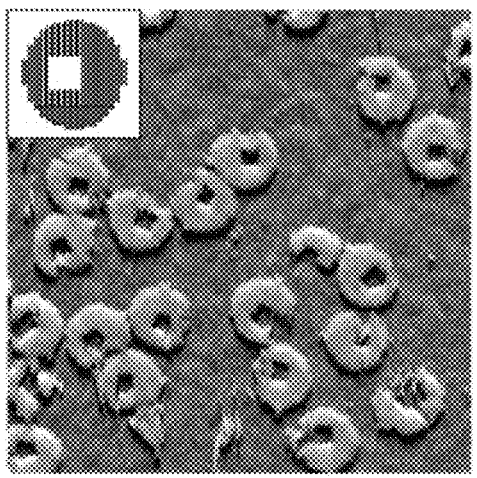
FIG. 13B depicts the shape of a binding site according to one embodiment of the present invention.

According to some embodiments of the present invention, the biasing of the surfaces (or faces) of the DNA origami to configure the faces to be binding and non-binding faces is combined with the orientation control through the disk with offset hole shape of the origami. FIG. 13A depicts an example of a DNA origami having the shape of a disk with a square (or rectangular) offset hole according to one embodiment of the present invention. As shown in FIG. 13A, the origami is approximately 101 nm long along its orientation axis (pointing vertically in FIG. 13A) and about 104 nm wide perpendicular to its orientation axis. The hole is about 30 nm long along the orientation axis and 31 nm wide perpendicular to the orientation axis. FIG. 13B depicts the shape of a binding site according to one embodiment of the present invention. As shown in FIG. 13B, the binding site is approximately 104 nm in diameter and has an offset hole with a radius of about 20 nm and may be patterned onto the surface of a substrate using electron beam lithography.

Figure 13C:
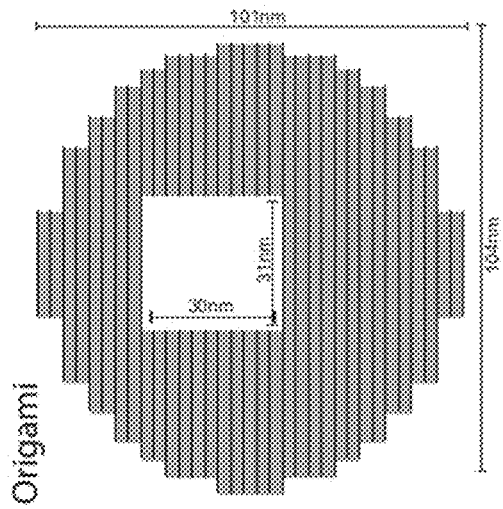
FIG. 13C is an AFM image of DNA origami according to one embodiment of the present invention having a shape of a disk with an offset hole on an unpatterned $SiO_2$ surface.

FIG. 13C is an AFM image of DNA origami according to one embodiment of the present invention having a shape of a disk with an offset hole on an unpatterned $SiO_2$ surface. The staples of the DNA origami depicted in FIG. 13C are all modified with 20 nucleotide poly(T) extensions, but the $D_1$ symmetry of the DNA origami prevents a determination of whether they are landing right-side up (with 20 nt extensions pointing up) or up-side down (with the 20 nt extensions facing the surface of the substrate).

Figure 13D:
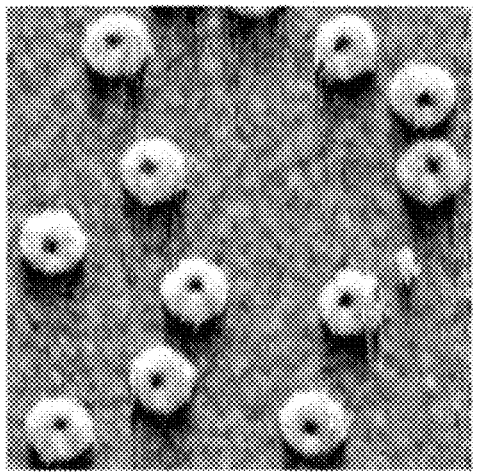
FIG. 13D is an AFM image of a modified version of the DNA origami the shape of a disk with an offset hole according to one embodiment of the present invention, where the modified DNA origami has a region of staples (red) which were omitted to break the $D_1$ symmetry of the shape.

FIG. 13D is an AFM image of a modified version of the DNA origami the shape of a disk with an offset hole according to one embodiment of the present invention, where the modified DNA origami has a region of staples (red) which were omitted to break the $D_1$ symmetry of the shape, as shown in the inset. This modified DNA origami was designed to help verify that the DNA origami bind to the $SiO_2$ substrate right-side up (with the 20 nt extensions on the face facing away from the substrate) by making it possible to determine which side of the DNA origami is facing up based on which edge of the origami looks ragged or broken. Green shading in FIG. 13D indicates origami which were judged to be right-side up. Of the 642 origami inspected in an experiment, 95.6% (614) were found to be right-side up; 4.4% were found to be upside-down or their orientation could not be determined.

Figure 14A:
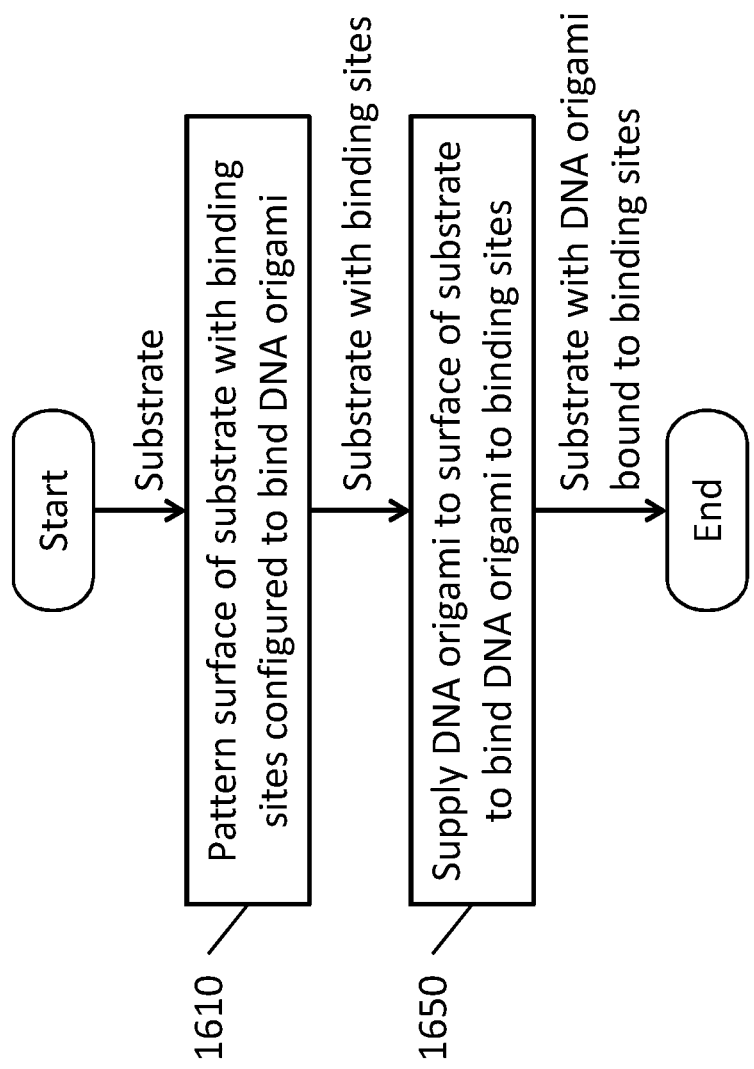
FIG. 14A is a flowchart of a method according to one embodiment of the present invention for fabricating an apparatus that includes DNA origami bound to a substrate.

Aspects of embodiments of the present invention relate to methods for making an apparatus that includes DNA origami bound to a substrate. FIG. 14A is a flowchart of a method according to one embodiment of the present invention for fabricating an apparatus that includes DNA origami bound to a substrate. However, embodiments of the present invention are not limited thereto, and encompass other techniques for fabricating devices by binding asymmetric DNA origami onto shape-matched binding sites.

Referring to FIG. 14A, in one embodiment of the present invention, in operation 1610, the surface of a substrate is patterned with binding sites configured to bind to DNA origami. However, as noted above, embodiments of the present invention are not limited to DNA origami, and in this flowchart, "DNA origami" (referring to scaffolded DNA origami) may be replaced with any other polynucleotide platform, such as single-stranded DNA tiles (DNA bricks), or single-stranded RNA origami. In embodiments of the present invention in which the binding sites have a rotationally asymmetric shape (such as the disk with offset hole shape, as discussed above), each binding site may have an orientation direction (a "first orientation direction") defined relative to an axis of rotation that is perpendicular to the surface of the substrate. Similarly, the molecular shape (e.g., DNA origami) having a shape corresponding to the binding site may also have an orientation direction (a "second orientation direction") defined relative to an axis of rotation that is perpendicular to the surface of the substrate when the molecular shape is on the surface of the substrate. A molecular shape may be referred to as being "aligned" with a binding when the first orientation of the binding site is in substantially same direction (same angle) as the second orientation of the molecular shape with respect to a frame of reference of the substrate.

Figure 14B:
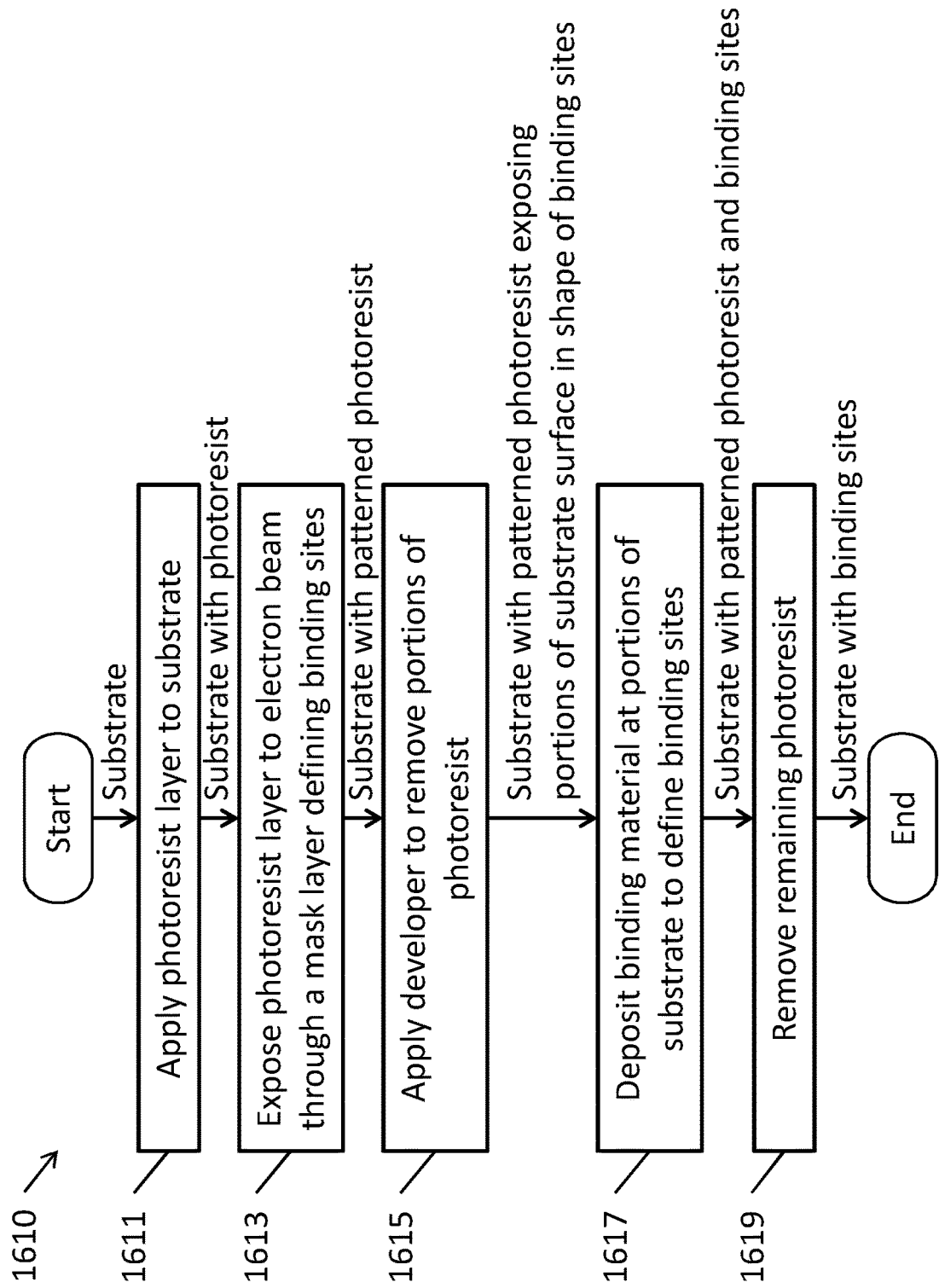
FIG. 14B is a flowchart of a method according to one embodiment of the present invention for patterning a substrate with binding sites configured to bind to DNA origami.

Each binding site patterned onto the surface of the substrate in operation 1610 may be patterned independently. For example, different binding sites may have the same orientation direction (e.g., same angle with respect to a reference frame of the substrate) or may have different orientation directions, where the orientation directions of the binding sites are defined by the patterning process. In addition, two different binding FIG. 14B is a flowchart of a method according to one embodiment of the present invention for patterning a substrate with binding sites configured to bind to DNA origami. In some embodiments, in which an unmodified substrate has medium or strong attraction to the binding or nonbinding face of a DNA origami, then the substrate may be first entirely modified to become a nonbinding background surface. In some embodiments, such as those with at least a thin layer of oxide on top (e.g. silicon dioxide or silicon nitride) the substrate is vapor-silanized with hexamethyldisilazane (HMDS) to create trimethyl silyl groups or solution-silanized with PEG-silane. Next, in operation 1611, the substrate is coated with a positive photoresist layer. In operation 1613, a patterned mask is applied to the surface of the substrate, where the pattern of the mask exposes the portions of the substrate in the shapes of the binding sites. (In the case of a negative photoresist layer, the mask exposes the portions of the substrate other than those that will form the binding sites). The mask independently defines the position and orientation of each binding site patterned onto the surface of the substrate. A light, such as ultraviolet light, or an electron-beam is directed toward the substrate, and the portions of the photoresist that are exposed by the mask interact with the photons or electrons. In operation 1615, the mask is removed and photoresist developer is applied to remove portions of the photoresist corresponding to the binding sites. In operation 1617, a physical process is applied or a chemical binding material is applied to the portions of the substrate corresponding to the binding sites.

In some embodiments alternative lithographic techniques are used to create the binding sites, including but not limited to: nanoim print lithography, microcontact or nanocontact printing, and dip-pen nanolithography (DPN). In such an embodiment, operation 1610 (shown in FIGS. 14A and 14B) is replaced with a protocol suitable for the alternative lithography. In embodiments where particularly large areas of silicon-family materials (silicon, silicon dioxide, silicon nitride, etc.) are to be patterned, nanoimprint lithography may be used. In embodiments where thiolated compounds are used as "inks" to create the binding sites and non-binding surfaces on gold, platinum or other noble metal substrates, micro/nanocontact printing and DPN may be used. In embodiments where pyrene compounds are used as inks to create binding sites and nonbinding surfaces on graphene, micro/nanocontact printing and DPN may be used. In embodiments where dithiolane compounds are used as inks to create binding sites and nonbinding sites on materials such as molybdenum disulfide, micro/nanocontact printing and DPN may be used.

As discussed above, in some embodiments of the present invention, the binding sites are made negative using silanols (see, e.g., FIG. 2) which are created during a physical process (an oxygen plasma etch) that removes a nonbinding layer formed of trimethyl silyl groups. In addition, as discussed above, the surface of the substrate may be chemically modified using a variety of functional groups such as: a carboxylate group (or other similarly negatively charged groups for indirect binding of negatively-charged DNA shapes via a positively charged divalent cation such as $Mg^{2+}$ or $Ni^{2+}$ or higher trivalent or polyvalent cations); an amine group (or other similar positively charged groups that directly bind negatively-charged DNA shapes); a thiol group (for coupling via disulfide bridges); gold or platinum (for binding DNA shapes functionalized with thiols, phosphorothioate backbones, poly-adenine or other single-stranded DNA extensions); or an attractive polymer coating (such as positively-charged poly-lysine), although embodiments of the present invention are not limited thereto. In one preferred embodiment binding sites are created by silanization with a carboxysilanes.

After the binding sites have been formed, the remaining photoresist in the masked areas is removed (stripped) in operation 1619 to complete the fabrication of a substrate with DNA origami binding sites. In some embodiments, such as those in which a nonbinding background was created before the photoresist was added in 1611, and the binding site was activated by an oxygen plasma etch, the binding site may be further enhanced by silanization with a carboxysilanes after the resist has been stripped.

In some embodiments of the present invention, the surface of the substrate is graphene or boron nitride (highly hydrophobic) or molybdenum disulfide ($MoS_2$, moderately to highly hydrophobic), and these materials must be patterned by different techniques to achieve the binding sites and nonbinding surfaces. In particular, graphene may be patterned using dip-pen nanolithography (Wang, Wechung M., et al., "Dip-Pen Nanolithography of Electrical Contacts to Single Graphene Flakes", ACS Nano 4, (2010): 6409-6416) in which a modifying agent is used as an ink and flowed down a microfabricated tip that is used to directly draw a pattern on the surface. The molecule pyrene binds noncovalently but strongly to graphene, and so modified pyrene molecules are commonly use functionalize the surface of graphene (e.g. Ghosh, Sujoy et al., "Effect of 1-Pyrene Carboxylic-Acid Functionalization of Graphene on Its Capacitive Energy Storage", J. Phys. Chem. C, 116 (2012):20688-20693). Thus in some embodiments one or more modified pyrenes may be used as an ink to create both binding sites and non-binding background substrate surfaces. DNA binding sites may be created with pyrene-carboxylic acids (for indirect binding via $Mg^{2+}$), or aminopyrene (for direct binding) applied from solvents such as dimethyl formamide (DMF). Nonbinding background surfaces may be created by application of a pyrene-PEG (polyethylene glycol). Essentially similar techniques may be used for molybdenum disulfide, except that analogous dithiolanes (cyclic disulfides that ring-open and bind to $MoS_2$) which may be used instead of pyrenes as taught in Canton-Vitoria, Ruben et al ("Functionalization of MoS2 with 1,2-dithiolanes: toward donor-acceptor nanohybrids for energy conversion" 2D Materials and Applications 1 (2017): 13). For pyrene or dithiolanes inks on graphene or molybdenum sulfide, respectively, micro/nanocontact printing may also be used to create binding sites and nonbinding surfaces.

Referring again to FIG. 14A, in operation 1650, DNA origami is supplied to the substrate surface, such as by flowing a solution of DNA origami over the binding sites on the surface of the substrate. As discussed above, according to some embodiments of the present invention, the DNA origami are modified such that each has a binding face biased to bind to the binding sites of the substrate more favorably than a non-binding face of the DNA origami. When the DNA origami reach the surface of the substrate with the binding face of the DNA origami facing the substrate, the asymmetric DNA origami translate and rotate along the plane of the substrate to align their orientations with the shape-matching binding sites in accordance with maximizing the binding energy (see, e.g., FIG. 8, above). DNA origami that approach the substrate with a different face (e.g., the non-binding face) facing the substrate, may fail to bind to the substrate, or weakly bind and release.

In embodiments where rotational control is applied to break rotational symmetry, it is important that the interaction between the binding face of the origami and the binding site be somewhat reversible, so that the asymmetric origami can readjust from its initial orientation on the binding site to the desired and final orientation. If the interaction is too strong, the origami may get stuck in an incorrect orientation. Thus for such embodiments, noncovalent interactions, such as weak electrostatic interactions, or weak hydrophobic/aromatic/stacking interactions may be preferred. In embodiments for which it is only important that the up/down symmetry of binding be broken, it is not necessary that interaction between the binding face of the origami and the binding site be irreversible, so stronger interactions such as disulfide bridges and covalent interactions may be used or even preferred.

Figure 14C:
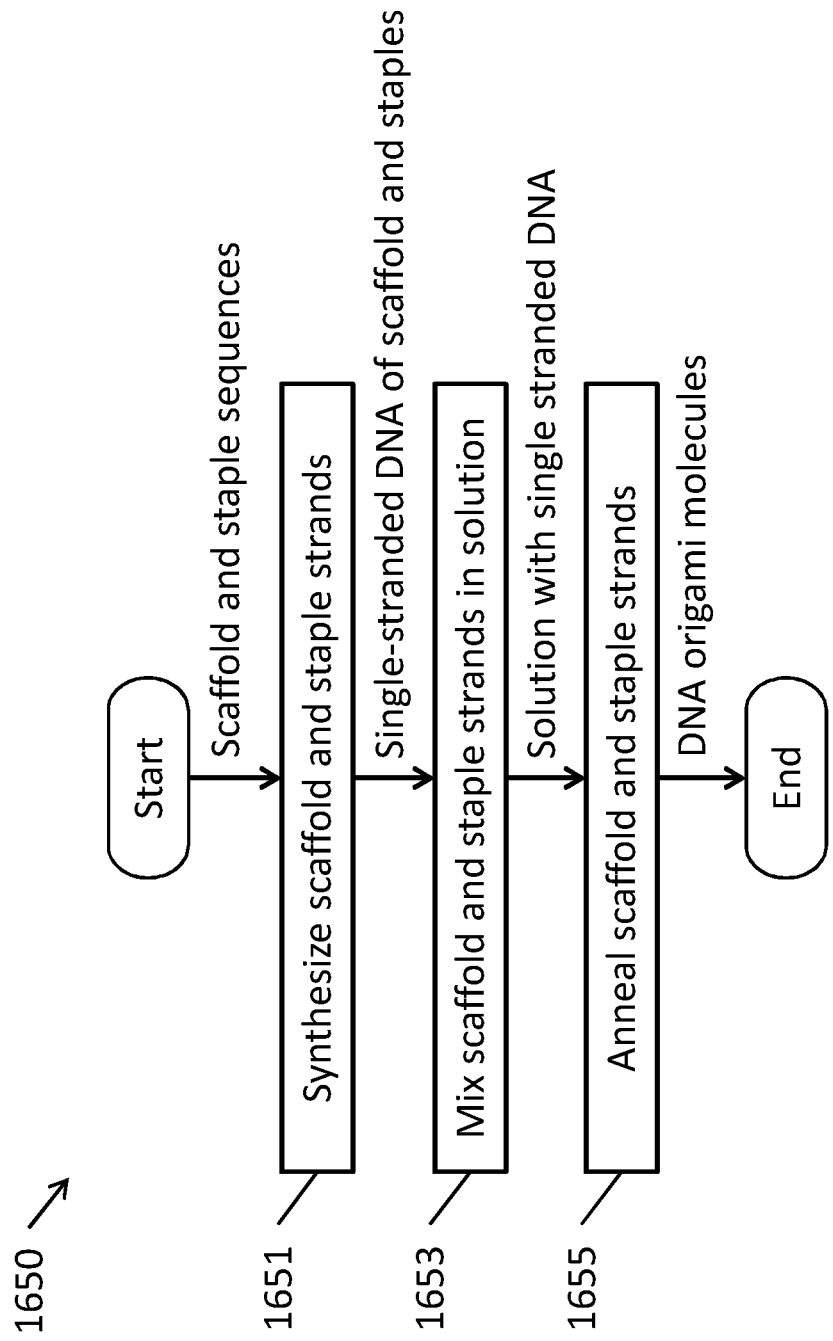
FIG. 14C is a flowchart of a method for making DNA origami according to one embodiment of the present invention.

FIG. 14C is a flowchart of a method for making DNA origami according to one embodiment of the present invention. Techniques for making DNA origami are described in, for example, Rothemund, Paul WK. "Folding DNA to create nanoscale shapes and patterns." *Nature* 440.7082 (2006): 297 and Supplementary Notes, the entire disclosures of which are incorporated by reference herein. To summarize, in operation 1651, single-stranded DNA is synthesized from a given scaffold sequence and rationally designed staple sequences. The scaffold sequence may be, for example, M13 phage single-stranded DNA. The sequences of the staple strands may be rationally designed using modeling software such as caDNAno (see, e.g., Douglas, Shawn M., et al. "Rapid prototyping of 3D DNA-origami shapes with caDNAno." *Nucleic acids research* 37.15 (2009): 5001-5006.), where the modeling software generates the sequences of the staple strands based on the sequences of the scaffold strand at the portions of the scaffold strand that are to be "stapled" together. Accordingly, a user can supply a target desired theoretical shape to the modeling software (e.g., a disk with a "yin-yang" or curved teardrop shaped hole) and the modeling software can compute sequences of strands that make up the desired molecule approximating the given shape. The single-stranded DNA staple strands and scaffold strands may be synthesized using standard oligonucleotide synthesis techniques and scaled up using polymerase chain reaction (PCR).

In operation 1653, the single stranded scaffolds and staple strands are mixed in solution such as Tris-Acetate-EDTA (TAE) buffer with 12.5 mM magnesium acetate (pH=8.3). In operation 1655, the scaffold and staple strands in the solution are annealed, such as through controlled heating and subsequent cooling of the solution from 95° C. to 20° C. in a PCR machine. The result is a solution containing the designed DNA origami molecules.

As noted above, one or more of the faces of the DNA origami (or other polynucleotide platform) may be modified in order to bias one side more strongly toward binding to binding sites on the surface of the substrate. The modifications may be made to the staple strands prior to the assembly of the DNA origami. As discussed above, in some embodiments of the present invention, the staple strands are modified with 20 nt poly(T) extensions, such that the extensions extend from one of the faces of the DNA origami. In addition, as discussed above, other modifications to appear on one face of the DNA origami include adding: a hydroxyl group; a carboxyl group; a polymer coating (e.g., DNA, polyethylene glycol or PEG, poly-L-lysine or PLL or poly (N-isopropylacrylamide) (PNIPAM); an amine; a thiol; or combinations thereof to the staple strands at locations such that the modifications are on one face of the DNA origami, thereby biasing one of the faces of the DNA origami to bind to the binding site of the surface of the substrate.

Other embodiments of the present invention replace operation 1650 (shown in FIGS. 14A and 14C) with the standard protocols from the literature for other polynucleotide platforms. Depending on the specific polynucleotide platform, modifications of the shape to provide for breaking up/down symmetry, and adding functional devices to the platform will either be very similar to the embodiment using DNA origami, or may be somewhat different. For example, for the embodiment using single-stranded DNA tiles (DNA bricks), the single stranded tiles can be modified analogously to the staples of DNA origami, to add polyT extensions to break up/down symmetry, or to add linkers (such as biotin, thiols, maleimide, primary amines, alkynes, etc.) as attachment points for devices. However, for shapes based on a polynucleotide platform, other techniques are required. For the embodiment using single-stranded RNA origami, up/down symmetry may be broken by inserting unstructured loops of RNA at positions on one side of the structure. To add devices to single-stranded RNA origami, a variety of RNA aptamer sequences (which could bind a particular small molecule), or RNA protein-binding domains (which can bind a specific protein) can be inserted into the structure to provide adaptors to bind devices. Devices can then be labelled with the appropriate small molecule or protein, which will bind to the RNA origami at desired locations.

Accordingly, aspects of embodiments of the present invention provide systems and methods for precise and reliable alignment of nanoscale devices on a substrate. In particular, aspects of embodiments of the present invention enable the control of the absolute position and orientation of a DNA origami molecule on the substrate of a surface, including which face of the DNA origami is bound to the substrate.

FIG. 15 depicts comparisons of different methods for aligning nanoscale devices that include, or are templated on, DNA strands, carbon nanotubes, metal nanowires, and DNA origami. FIG. 15 focuses on asymmetric particles (e.g., non-spherical particles), because orientation control is less relevant to symmetric (e.g. spherical) particles. FIG. 15A depicts simple flow powered by the receding meniscus of an evaporating drop, often termed molecular combing, which has been used to arrange DNA and other one-dimensional DNA nanostructures, aligning them to a single orientation (θ), at least locally. This technique has also been used to align inorganic nanowires, but allows 180° rotation and spin along the long axis of the one dimensional nanostructures.

Figure 15A:
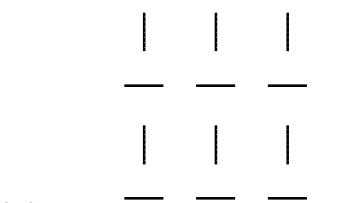
FIG. 15A depicts simple flow powered by the receding meniscus of an evaporating drop, often termed molecular combing, which has been used to arrange DNA and other one-dimensional DNA nanostructures, aligning them to a single orientation ($\theta$), at least locally.
Figure 15B:
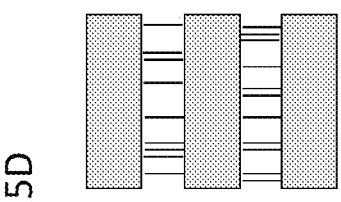
FIG. 15B depicts that, combined with microfluidics, shear from moving experimental setups, and a variety of stamping and pattern-transfer methods, flow alignment can be made considerably more powerful, and can allow allowing limited to no control over the x-y positioning of one dimensional nanostructures.

FIG. 15B depicts that, combined with microfluidics, shear from moving experimental setups, and a variety of stamping and pattern-transfer methods, flow alignment can be made considerably more powerful, and can allow allowing limited to no control over the x-y positioning of one dimensional nanostructures. Furthermore, like the technique of FIG. 15A, this technique allows 180° rotation and spin along the long axis of the one dimensional nanostructures. While a single application is still limited to a single orientation (θ), multiple applications can lead to arrays of crossed structures. Similar results can be achieved with other techniques such as Langmuir Blodgett films.

Figure 15C:
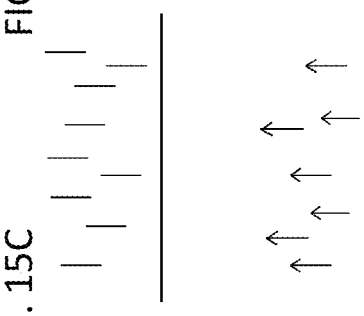
FIG. 15C depicts the use of magnetic and electric fields to align carbon nanotubes and metallic nanowires, and particulate dumbbells.

FIG. 15C depicts the use of magnetic and electric fields to align carbon nanotubes and metallic nanowires, and particulate dumbbells. In these examples, alignment forces act on induced dipoles, devices so aligned are subject to random 180° rotation. However, this technique provides no x, y positional control and allows spin along the long axis of the nanostructures. Alignment of fixed dipoles, for example the electrostatic dipoles of antibodies, or the magnetic dipoles of microfabricated helical swimmers, allow rotational symmetry to be broken.

Figure 15D:
FIG. 15D depicts a combination of chemical differentiation (via e-beam activation) and flow alignment can achieve orientation (up to 180° rotation) and some control over position (e.g., in they direction but not the x direction, as shown in FIG. 15D).

FIG. 15D depicts a combination of chemical differentiation (via e-beam activation) and flow alignment can achieve orientation (up to 180° rotation) and some control over position (e.g., in they direction but not the x direction, as shown in FIG. 15D).

Figure 15E:
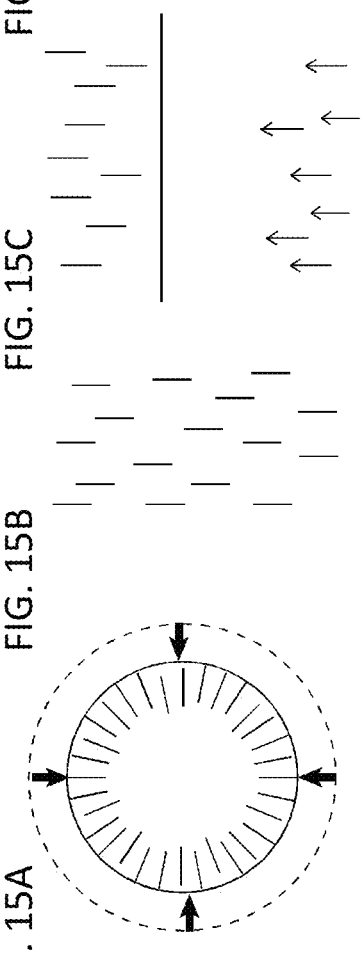
FIG. 15E depicts scanning probe-based chemical differentiation of a surface (here dip-pen nanolithography) allows linear viruses or carbon nanotubes to be oriented arbitrarily, although it allows 180° rotation and spin around the long axis of the linear virus or linear carbon nanotubes.

FIG. 15E depicts scanning probe-based chemical differentiation of a surface (here dip-pen nanolithography) allows linear viruses or carbon nanotubes to be oriented arbitrarily, although it allows 180° rotation and spin around the long axis of the linear virus or linear carbon nanotubes.

Figure 15F:
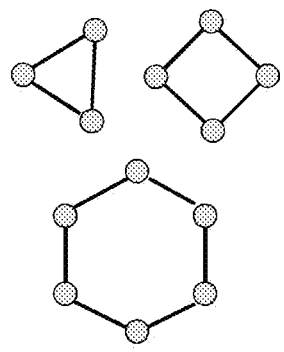
FIG. 15F depicts lithographic patterning of gold dots allows linear DNA structures terminated with thiols to be arbitrarily oriented, and similar work on block copolymers, compromises arbitrary x, y, θ control for potential scalability, but also allows 180° rotation and spin along the long axis of the linear DNA structures.

FIG. 15F depicts lithographic patterning of gold dots allows linear DNA structures terminated with thiols to be arbitrarily oriented, and similar work on block copolymers, compromises arbitrary x, y, θ control for potential scalability, but also allows 180° rotation and spin along the long axis of the linear DNA structures.

Figure 15G:
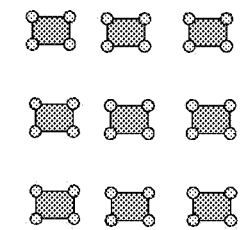
FIG. 15G illustrates the extension of the gold-dot/thiol approach of FIG. 15F to two-dimensional nanostructures (rectangles), thereby allowing orientational freedom to be limited to four degenerate orientations (e.g., allows arbitrary x, y, 8 control, although the 8 can only be controlled to one of four different orientations).

FIG. 15G illustrates the extension of the gold-dot/thiol approach of FIG. 15F to two-dimensional nanostructures (rectangles), thereby allowing orientational freedom to be limited to four degenerate orientations (e.g., allows arbitrary x, y, θ control, although the θ can only be controlled to one of four different orientations).

Figure 15H:
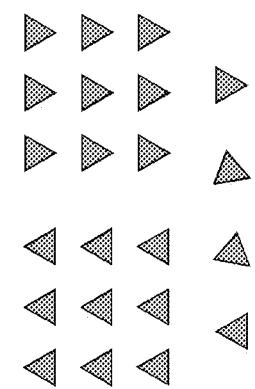
FIG. 15H depicts DNA origami placement of equilateral triangles still leaves six degenerate orientations, and orientational fidelity is relatively coarse, allowing only four rotations to be distinguished, because the alignment is only to within ±10°.

FIG. 15H depicts DNA origami placement of equilateral triangles still leaves six degenerate orientations, and orientational fidelity is relatively coarse, allowing only four rotations to be distinguished, because the alignment is only to within ±10°.

Figure 15I:
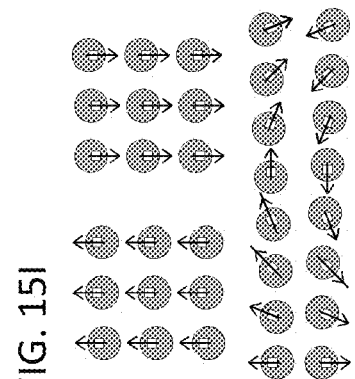
FIG. 15I depicts DNA origami having the shape of a disk with offset hole according to embodiments of the present invention achieves absolute and arbitrary orientation, and should enable more than 50 distinguishable rotations, because initial experimental results have shown that alignment to within ±3.2°.

FIG. 15I depicts DNA origami having the shape of a disk with offset hole according to embodiments of the present invention achieves absolute and arbitrary orientation, and should enable more than 50 distinguishable rotations, because initial experimental results have shown that alignment to within ±3.2°.

Figure 16:
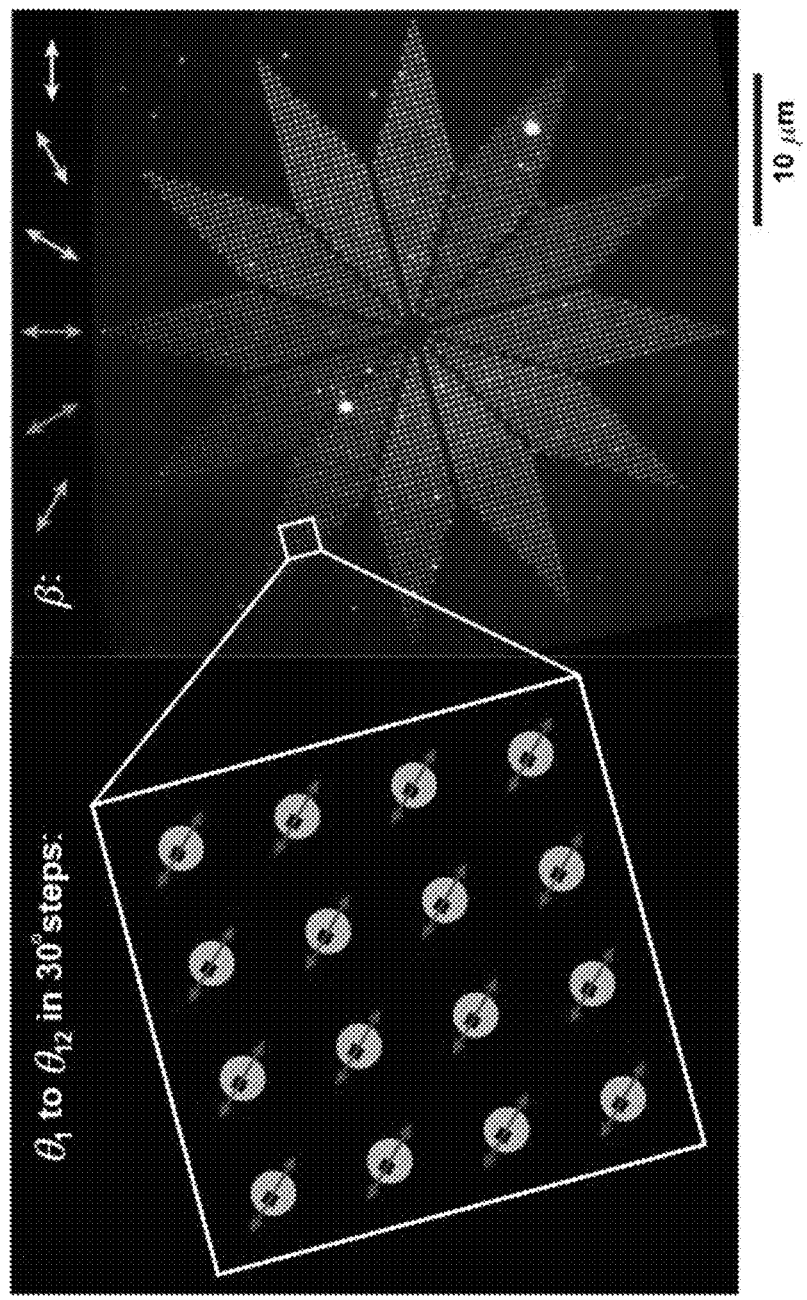
FIG. 16 depicts a two-dimensional polarimeter composed of 3,456 DNA origami according to one embodiment of the present invention with fluorescent dye intercalated therein, where the polarimeter is divided into twelve (12) rhomboidal arrays, the DNA origami in a given array having a same orientation direction (θ), the arrays having orientation directions graduated in 30° steps.

As discussed above, some aspects of embodiments of the present invention relate to organizing light emitting dipoles on a surface. Organization of light emitting dipoles on a surface may have a number of practical applications. As one example, FIG. 16 depicts a two-dimensional polarimeter composed of 3,456 DNA origami according to one embodiment of the present invention with fluorescent dye intercalated therein, where the polarimeter is divided into twelve (12) rhomboidal contiguous arrays, the DNA origami in a given array having a same orientation (θ) due to the binding sites in each array having the same orientation (an "array orientation"), the arrays having orientations graduated in 30° steps. FIG. 16 shows the combination of six different exposures to polarized light at polarization angles β, where each different polarization angle is represented in FIG. 16 with a different color, and the response from the DNA origami to a given polarization are shown with corresponding colors. As seen in FIG. 16, the polarization of light irradiated onto a polarimeter in accordance with embodiments of the present invention can be determined based on which of the twelve rhomboidal arrays emit light in response to the input light.

Figure 17:
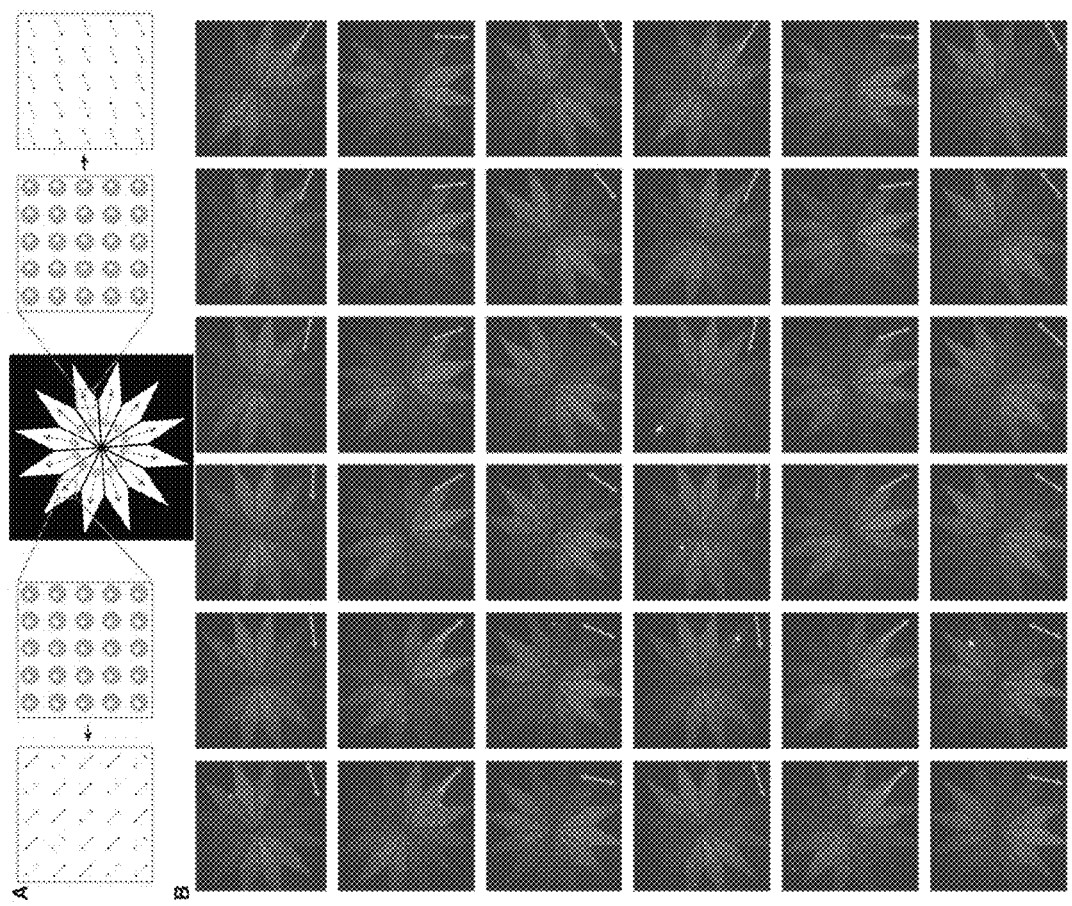
FIG. 17 depicts a combination of 36 fluorescence images of a two-dimensional polarimeter composed of DNA origami in accordance with one embodiment of the present invention, where the images are colored according to polarization angle β enables six polarizations to be distinguished by eye.

FIG. 17 depicts a combination of 36 fluorescence images of a two-dimensional polarimeter composed of DNA origami in accordance with one embodiment of the present invention, where the images are colored according to polarization angle β enables six polarizations to be distinguished by eye. FIG. 17A shows the orientation of disk with offset hole shaped DNA origami in each of the 12 rays of the polarimeter. The DNA helices are arranged perpendicular to the ray and so the excitation dipole of intercalated TOTO®-3 is aligned parallel to the ray. FIG. 17B shows thirty-six (36) images of the polarimeter under polarized illumination; green arrows indicate axis of polarization.

Some aspects of embodiments of the present invention are directed to hybrid devices that combine self-assembled nanostructures, such as quantum dots, carbon nanotubes or molecules with microfabricated devices like optical resonators or transistors to obtain devices or apparatuses ranging from biosensors to light sources for on-chip quantum information processing. The performance (e.g. sensitivity of a detector, or intensity of a light source) of such devices depends on the strength of the coupling between the emitter and resonator. In particular, emission intensity is proportional to the cavity Purcell enhancement $F_{cav} \propto |\mu \cdot E(r)|^2$, which is typically a sensitive function of the position of the emitter r and the orientation of the emission dipole μ relative to the cavity electric field E. To maximize coupling, the emitter should be positioned in a peak of a resonant mode, with emission dipole μ aligned to the polarization of electric field E at position r. However, it is difficult to fabricate resonators with emitters that are both precisely positioned and precisely aligned using comparative techniques. Most of these approaches for positioning involve randomly growing or depositing emitters on a surface, selecting emitters with microscopy, and fabricating resonators around them. Some emitters can be grown at predetermined sites within resonators, but in general, deterministic approaches for positioning emitters rely on scanning probe microscopy. Neither "select and post-process" nor scanning probe approaches can scale to large numbers of devices, or provide deterministic alignment. Conversely, methods for achieving deterministic alignment of molecular or vacancy-based emitters do not address positioning. DNA origami placement has previously been used to achieve the large-scale positioning of molecular emitters within L3 photonic crystal cavities (PCCs).

Fluorescent dye (e.g., TOTO®-3) intercalated DNA origami in accordance with embodiments of the present invention enables control the alignment θ of an emission dipole μ in the cavity.

To optimize emission from the photonic crystal cavities, in one embodiment of the present invention, a 13×6 array of identical resonators was built (see FIGS. 19 and 20) with DNA origami positioned and oriented in the center of a y-polarized peak in E, and varied θ in 13 steps from 90° to −90° across the width of the array.

Figure 18:
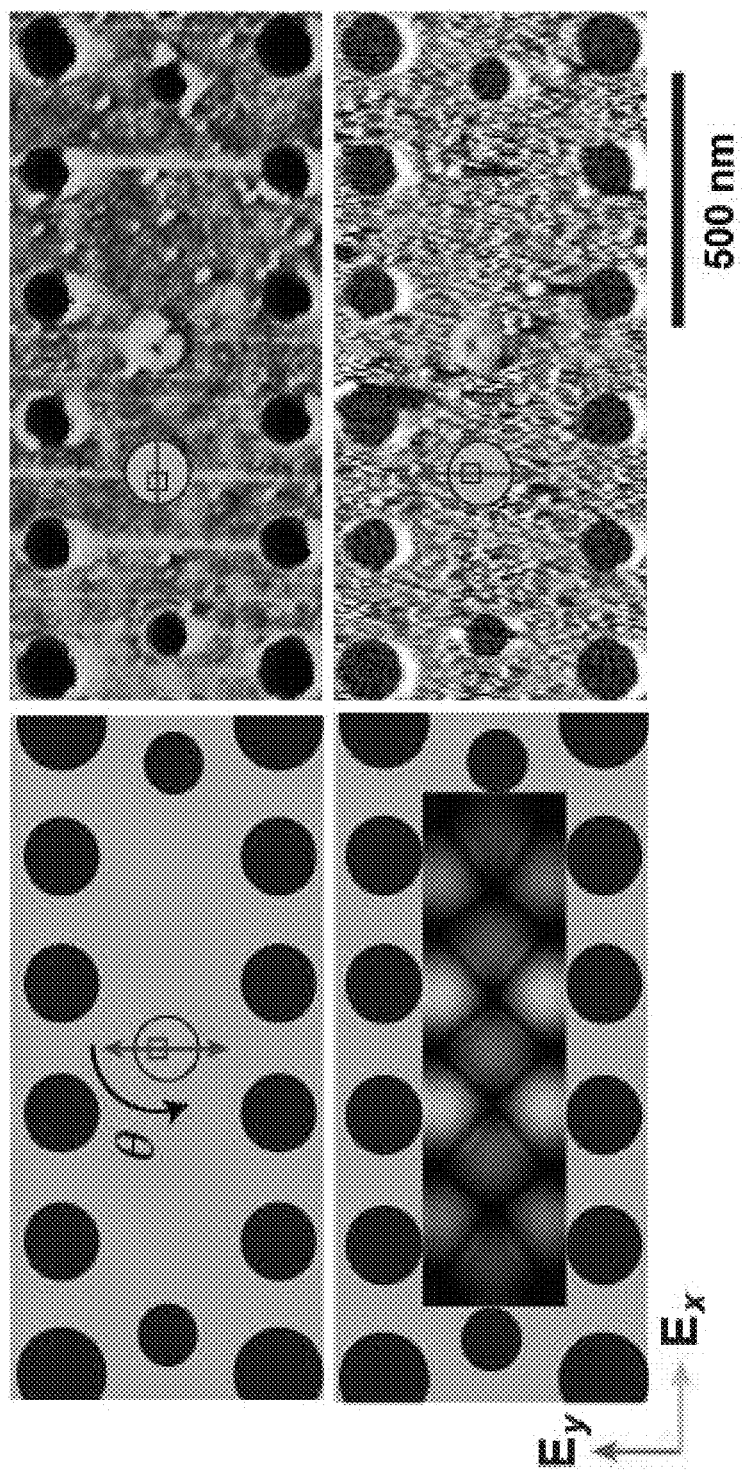
FIG. 18 depicts schema, simulation, and AFM images for coupling between TOTO®-3 emitters and photonic crystal cavities (PCCs) as a function of origami rotation θ according to one embodiment of the present invention.

FIG. 18 depicts schema, simulation, and AFM images for coupling between TOTO®-3 emitters and PCCs as a function of origami rotation θ. Ey (purple) and Ex (blue) label polarization for finite-difference time-domain (FDTD) simulation of the electric field. Red axes show polarization of peak TOTO®-3 emission.

FIGS. 19A through 19N are a schematic illustration of a process flow for fabricating PCC arrays according to one embodiment of the present invention. Although FIGS. 19A through 19N show that SiN is used on both sides (top and bottom), embodiments of the present invention are not limited thereto and wafers with SiN on a single side may also be used. As shown in FIG. 19A, the process begins with a clean SiN/Si/SiN wafer (as noted above, embodiments of the present invention are not limited thereto and may also use, for example, an Si/SiN wafer). In FIG. 19B, photoresist (e.g., ZEP from Nippon Zeon Corporation) is spin coated onto the back side of the wafer. in FIG. 19C, the photoresist is patterned, developed, and a dry etch is used to remove the exposed portions of the SiN and part of the Si. In FIG. 19D, the Si layer is anisotropically etched with KOH to leave thin Si support. In FIG. 19E, alignment markers are defined on the top surface of the structure by removing the SiN and a portion of the Si layer at locations adjacent the cavity etched into the bottom of the structure. In FIG. 19F, the structure is plasma cleaned, dehydrated, silanized to create trimethyl silyl groups, and baked to stabilize. In FIG. 19G, photoresist is spin coated onto the top of the structure. In FIG. 19H, an electron beam is used to pattern the DNA origami binding sites (e.g., having the disk with offset hole shape) onto the photoresist, and the photoresist is developed. In FIG. 19I, $O_2$ plasma etching is used to create surface silanols on the binding sites. In FIG. 19J, the silanols are converted to carboxyl groups via carboxyethylsilanetriol sodium salt (CTES) silanization. In FIG. 19K, the photoresist previously deposited on the top of the structure (see FIG. 19G) is removed and new photoresist is spin deposited on the top side of the structure. In FIG. 19L, the alignment markers are used as reference points to write (e.g., using an electron beam) the photonic crystal cavities around the origami binding site, and the photoresist is developed. In FIG. 19M, the SiN layer is etched away. In FIG. 19N, the thin Si support is etched using $XeF_2$ and the top resist is stripped away, leaving a fabricated structure. After fabrication, the substrates are incubated in origami solution, rinsed of excess origami, subject to an ethanol dilution series, and air dried, thereby forming an apparatus with a DNA origami molecule, carrying at least one emission dipole (the TOTO®-3 dye), precisely placed within the PCC.

Figure 20A:
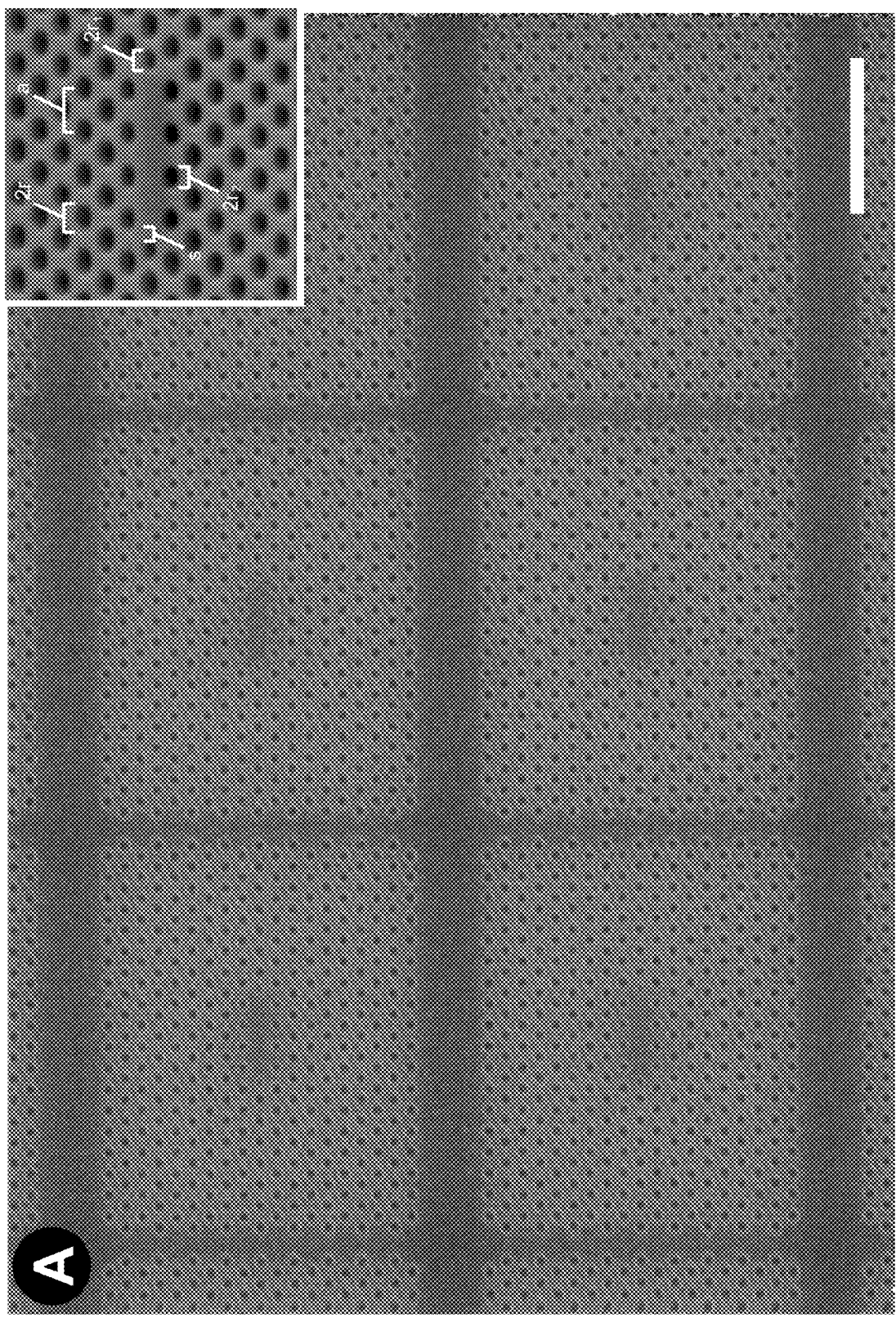
Figure 20B:
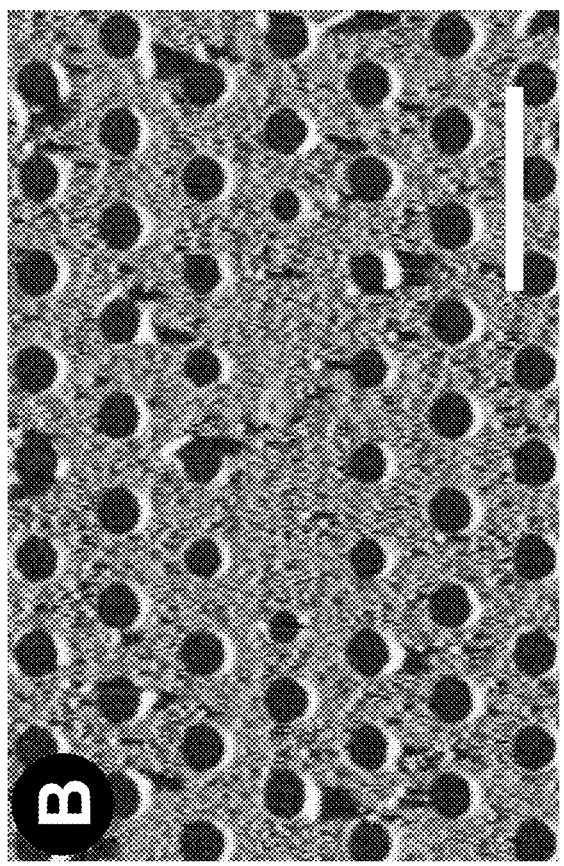
FIG. 20B is an atomic force microscopy (AFM) image of a PCC with a single DNA origami having a disk with offset hole shape, oriented with its DNA helices parallel to the long axis of the cavity.
Figure 20C:
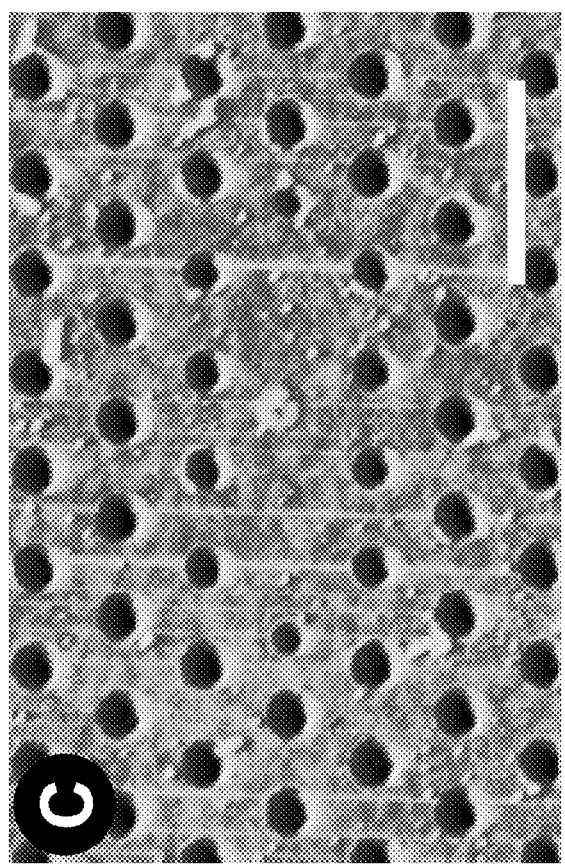
FIG. 20C is similar to FIG. 20B, with its DNA origami oriented so that its helices are perpendicular to the long axis of the cavity. The scale bars for FIGS. 20B and 20C are 500 nm.

FIG. 20 includes images of photonic crystal arrays according to some embodiments of the present invention. FIG. 20A is a scanning electron microscopy (SEM) image of a section of the 13×6 PCC array described above, where the scale bar is 2 µm. The inset shows critical dimensions of different features of the PCC: a=256 nm, r/a=0.3, $r_1$/a=0.2, $r_2$/a=0.25, s=0.22a. FIG. 20B is an atomic force microscopy (AFM) image of a PCC with a single DNA origami having a disk with offset hole shape, oriented with its DNA helices parallel to the long axis of the cavity. FIG. 20C is similar to FIG. 20B, with its DNA origami oriented so that its helices are perpendicular to the long axis of the cavity. The scale bars for FIGS. 20B and 20C are 500 nm.

Figure 21:
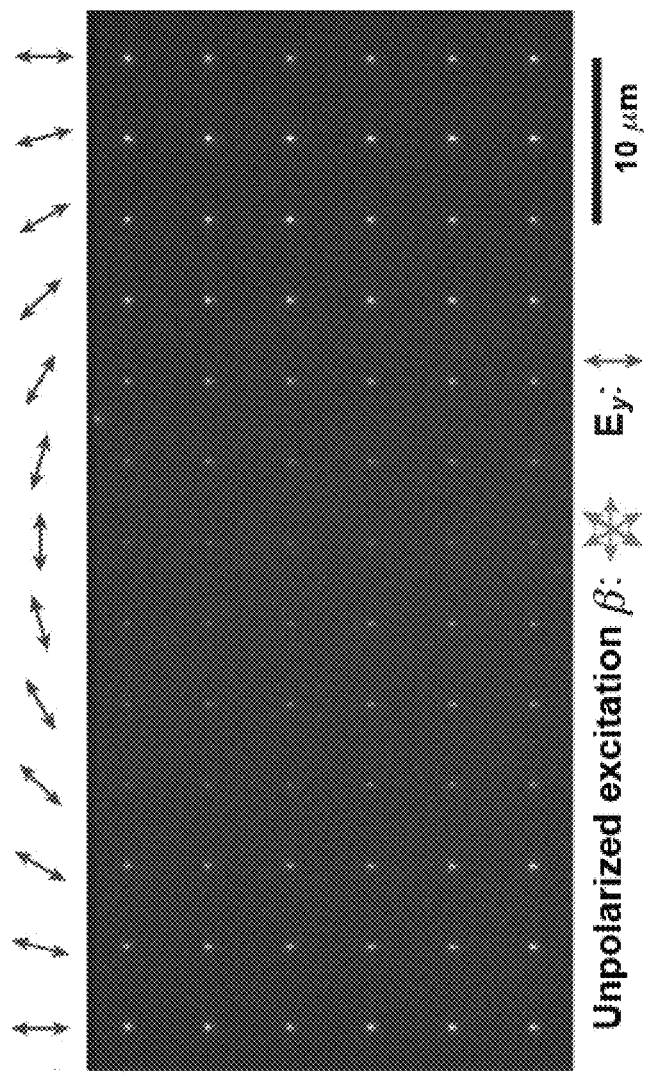
FIG. 21 shows the fluorescence of a photonic crystal cavity array with varying origami orientation direction θ according to one embodiment of the present invention, excited by unpolarized light β.
Figure 22:
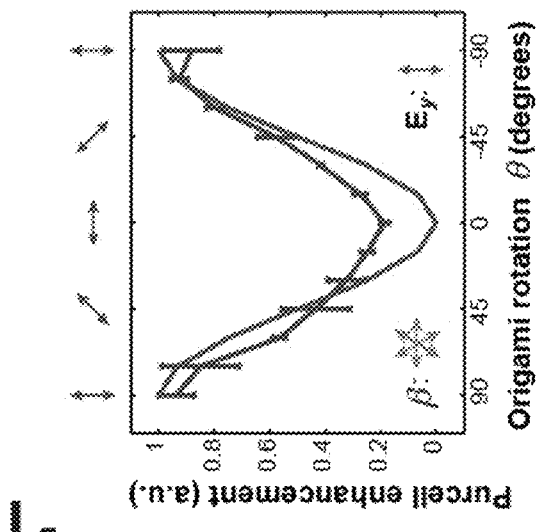
FIG. 22 depicts data (red) from FIG. 21 and simulation (blue), where the error bars indicate ±1SD for N=6.

FIG. 21 shows the fluorescence of a photonic crystal cavity array with varying origami orientation θ, excited by unpolarized light Maximum coupling is observed when the DNA origami align TOTO®-3 emission dipoles with $E_y$. FIG. 22 depicts data (red) from FIG. 21 and simulation (blue), where the error bars indicate ±1SD for N=6.

Emission intensity roughly followed the expected $\cos^2(\theta)$ relationship described above, and a 4.5-fold increase was observed for θ which maximally align TOTO®-3 dipoles with $E_y$. Potential reasons for disagreement between experimental intensity at 0° with FDTD simulation of a single dipole are similar to those described for bleed-through above: TOTO®-3 dyes are spread out over the 100 nm diameter disk of the DNA origami rather than in the exact center of the cavity, φ≠90 contributes to a net dipole strength parallel to $E_x$, and alignment error.

Beyond emitter-in-cavity devices, the ability of embodiments of the present invention to simultaneously position and orient molecular and nanoparticle components are also applicable to nanophotonics. The collective behavior of multiple emitter systems is highly sensitive to inter-emitter distance and relative dipole orientation, therefore, embodiments of the present invention are applicable to studying and engineering fundamental phenomena such as superradiance, and other coherence effects. Positioning and orientation of molecular emitters within optical nanoantennas using embodiments of the present invention will allow antenna performance to be optimized; similar control over metal nanoparticle dipoles will enable optical nano-circuit elements to be programmed with series, parallel or intermediate behavior.

Some aspects of embodiments of the present invention relate to controlling density of active molecules on a surface. Due to the precise shape of the DNA origami as well as the ability to digitally accommodate DNA functionalized molecules (e.g., attached to the staple strands of the DNA origami), when the DNA origami are closely packed on the surface, embodiments of the present invention allow precise control the density of the DNA functionalized molecules on the surface. The designed density of molecules can be given by D=N/A, when N is the number of DNA functionalized molecules per DNA origami (e.g., attached to a specified subset of the staple strands) and A is the area of DNA origami. In comparative techniques, molecules could be close packed on a surface or randomly organized on a surface, neither of which allows control of the density of the molecules on the surface.

In many applications of biotechnology, it is not important to control the rotational orientation of a molecular device, such as an antibody, but rather it is important to control the density of the molecular devices on the surface of a substrate. In such cases, the aspect of the present invention which is most relevant to the application is the invention's ability to break up/down symmetry during deposition of a DNA origami such that the molecular devices are deposited in an functionally active state (e.g., not facing the substrate). For example, in one embodiment, it may be desirable to position single antibodies on a rectangular grid with 1-micron spacing between positions on the grid (or any fixed spacing of binding sites that can be created using lithography). In some such embodiments, an antibody is coupled to DNA origami and then applied to a grid of binding sites with 1-micron spacing. However, without the ability to break up-down symmetry, the resulting grid would have, on average, 50% of the antibodies facing down (and thus inactive) and 50% of the antibodies facing up (and thus active), in a random, non-uniform, and non-reproducible pattern. By using a biased origami with a binding face, a non-binding face, and an antibody bound to the non-binding face, then a 1-micron grid of antibodies can be created with 100% or nearly 100% of the antibodies facing up. This problem applies not to antibodies but any molecular entity that one might wish to pattern at a defined density on a surface, including arbitrary proteins, nucleic acids, other polymers, or small molecules including receptor ligands.

Accordingly, in some embodiments of the present invention, the molecular shape is not asymmetric, or the binding site is not asymmetric, or both the molecular shape and the binding site are not asymmetric, and so rotational symmetry is not broken, but up/down symmetry is broken. In such embodiments, a molecule of interest such as an antibody, arbitrary protein, nucleic acid or small molecule is attached to the non-binding face of the molecular shape, so that, when the molecular shape is deposited on a surface with binding sites, all or substantially all of the molecules of interest land face up, and their density on the surface is deterministically (non-randomly) controlled to correspond to the density that is set by the pattern of binding sites.

Creation of specific binding sites on a surface incurs some expense, even when performed with a low cost lithography such as nanoimprint lithography. In some applications it is important to be able to control the average density of a molecule of interest on a surface at extremely low manufacturing cost. Accordingly, some embodiments of the present invention may be used to control the density of a molecule on the surface without the fabrication of specific binding sites (e.g., without using a mask to pattern the substrate), such as using an unpatterned surface in which substantially the entire substrate or a large region may be considered a single large binding site that is large enough to bind multiple molecular shapes. In some such embodiments, the molecule of interest is attached to the non-binding face of the molecular shape (to create a "functionalized shape"), so that, when the molecular shape is deposited on a surface with one or more large binding sites according to some embodiments of the present invention, all (or substantially all) of the molecules of interest land face up. In such embodiments, the average density of molecules of interest on the surface can be set either by the concentration of the applied molecular shapes, or by the introduction of "dummy" molecular shapes which do not carry the molecule of interest. In the latter case, the average density of molecules of interest is set or controlled by the ratio of dummy shapes to functionalized shapes that are applied to the substrate. Such embodiments are expected to be useful when exceedingly low cost surface coatings are required, for example in the case that the molecule of interest whose density must be controlled is an anti-fouling compound, such as a neutral hydrophilic polymer or a zwitterionic compound.

While the present invention has been described in connection with certain exemplary embodiments, it is to be understood that the invention is not limited to the disclosed embodiments, but, on the contrary, is intended to cover various modifications and equivalent arrangements included within the spirit and scope of the appended claims, and equivalents thereof.

What is claimed is:

1. A structure comprising:
    a substrate having a patterned surface of one or more negatively-charged binding sites and a non-binding background; and
    a molecular shape comprising polynucleotides generated by a polynucleotide platform, the molecular shape being bound to one of the one or more binding sites,
    wherein the molecular shape comprises a plurality of faces comprising a binding face and one or more non-binding faces,
    wherein the binding face of the molecular shape has an outline that matches the outline of the one or more binding sites,
    wherein the non-binding face of the molecular shape comprises a plurality of modifications that are repellant to the binding site,
    wherein the majority of the binding face of the molecular shape has an unmodified phosphate backbone, and
    wherein, in the presence of a multivalent cation, the one or more binding sites have a higher binding affinity for the unmodified phosphate backbone of the binding face than for the one or more non-binding faces.

2. The structure of claim 1, wherein the patterned surface of the substrate at the one or more binding sites comprises:
    silanols;
    carboxylate groups;
    negatively charged functional groups;
    negatively charged polymers; or
    an inherent negative charge.

3. The structure of claim 1, wherein the modifications that are repellant to the binding site comprise at least one of:
    a plurality of single stranded DNA extensions;
    a neutral polymer;
    a zwitterionic coating; or
    combinations thereof.

4. The structure of claim 1, wherein the patterned surface of the substrate has a non-binding background comprising:
    trimethyl silyl groups;
    neutral functional groups;
    a neutral polymer;
    a zwitterionic coating; or
    combinations thereof.

5. The structure of claim 1, wherein the molecular shape has a shape corresponding to a shape of a binding site of the one or more binding sites.

* * * * *

UNITED STATES PATENT AND TRADEMARK OFFICE
CERTIFICATE OF CORRECTION

PATENT NO. : 11,125,748 B2
APPLICATION NO. : 16/121603
DATED : September 21, 2021
INVENTOR(S) : Ashwin Gopinath et al.

Page 1 of 1

It is certified that error appears in the above-identified patent and that said Letters Patent is hereby corrected as shown below:

In the Specification

Column 1, Line 22 after "14-1-0702" insert -- and N00014-17-1-2610 --

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*